United States Patent
Jiang et al.

(10) Patent No.: US 7,919,241 B2
(45) Date of Patent: Apr. 5, 2011

(54) POLYMORPHISMS IN FATTY ACID BINDING PROTEIN 4 ("FABP4") GENE AND THEIR ASSOCIATIONS WITH MEASURES OF MARBLING AND SUBCUTANEOUS FAT DEPTH IN BEEF CATTLE

(75) Inventors: Zhihua Jiang, Pullman, WA (US); Jennifer J. Michal, Albion, WA (US)

(73) Assignee: Washington State University Research Foundation, Pullman, WA (US)

( * ) Notice: Subject to any disclaimer, the term of this patent is extended or adjusted under 35 U.S.C. 154(b) by 532 days.

(21) Appl. No.: 11/442,626

(22) Filed: May 26, 2006

(65) Prior Publication Data
US 2007/0020658 A1    Jan. 25, 2007

Related U.S. Application Data

(60) Provisional application No. 60/690,408, filed on Jun. 13, 2005.

(51) Int. Cl.
*C12Q 1/68* (2006.01)
(52) U.S. Cl. .......................................................... 435/6
(58) Field of Classification Search ........................ None
See application file for complete search history.

(56) References Cited

OTHER PUBLICATIONS

Ye et al. 7th World Congress on Genetics Applied to Livestock Production, Aug. 19-23, 2002, Montpelier, France; four pages.*
Mummidi et al. The Journal of Biochemistry. vol. 275, No. 25, Issue of Jun. 23, pp. 18946-18961, 2000.*
Juppner Bone vol. 17, No. 2, Supplement Aug. 1995:39S-42S.*
Thisted. What is a P-value? The University of Chicago, 5841 South Maryland Avenue (MC 2007), Chicago, IL 60637. http://www.stat.uchicago.edu/~thisted. six pages.*
X. Ye et al., Polymorphisms of Histone Deacetylase 1 and 3 Genes and Fatty Acid Binding Protein 3 and 4 Genes and their Associations with Economic Traits in Swine, 7th World Congress on Genetics Applied to Livestock Production, Aug. 19-23, 2002, Montpelier, France, four pages.

* cited by examiner

*Primary Examiner* — Juliet C Switzer
(74) *Attorney, Agent, or Firm* — Judy Jarecki-Black; Chad Kitchen; Merial Limited

(57) ABSTRACT

The physiological regulation of intake, growth and energy partitioning in animals is under the control of multiple genes, which may be important candidates for unraveling the genetic variation in economically relevant traits in beef production. The present invention relates to the identification of single nucleotide polymorphisms (SNPs) within the bovine genes encoding fatty acid binding proteins and their associations with economically relevant traits in beef production. The invention further encompasses methods and systems, including network-based processes, to manage the SNP data and other data relating to specific animals and herds of animals, veterinarian care, diagnostic and quality control data and management of livestock which, based on genotyping, have predictable meat quality traits, husbandry conditions, animal welfare, food safety information, audit of existing processes and data from field locations.

2 Claims, 12 Drawing Sheets

A. G/C SNP at position 7516
A A A C C C G C T G C C A A  SEQ ID NO:6
A A A C C C C C T G C C A A  SEQ ID NO:7
B. G/C SNP at position 7713
GC AC AC AC AG AC AC AC AC AG ACAC AC AC AC AC AC AC  SEQ ID NO:8
GC AC AC AC AG AC AC AC AC AC AC AC AC AC AC AC AC AC  SEQ ID NO:9
FIG. 2

```
   1 GCAGCCAAAA ATGGAGAAGC TCTATACAGT CAGCAAAAAC AAGACTGGGA GCTGACTGTG
  61 GCTCAGATCA TGAGTTCCTT ATTGCCAAAT TCAGACTTAA ATTGAAGAAA GCAGGGAAAA
 121 CCACTAGACC ATTCAGGCAT GACCTAAATC AAAACAACAA CAACATGTCA TTATATTAAT
 181 ACTTTGTCCA AACACATGGA ACATATAATA CCAAAAGTGA ACCCTAAGGT AATATATGGA
 241 CTTTGAGTGA TTATAATATA CCAATATAGG TTCATTCTTA GTAAAAATTA CCATTCTGGT
 301 GAATGATATT GATAATGGGG GAGGCTATCC ATATGCGGGA ACAGGGAGTA CATGAGAAAT
 361 CTCTGTACTT TCCTCTCAAT TTTGTTATAA ACCTGAAACT TCTCTAAAAA ATTATCATAA
 421 AAGCAAAACA AACTAAAAAC AAAAGCCATT TATTAGTTTA GAACATGAAG TTATCCCTGT
 481 ATGAAACTTG ATCATTTTTA TTTTCTTGTT CGATGAATTC ATAATAGTAA GCCTACCCTG
 541 AATGGTACAT CACCCACAGT CTATAATATG TCTATGCAAC AGTTCAGACT GAATGATCAT
 601 TATCACTGTG CCGTTAACAT ATGCAACCAT TAAAAGTTAC TATTGTAACA CAACTTTACC
 661 CGTTTTCTT AGCAAATTTC ATGCCTACAG AAATCTGTC CTTTACGGAA TCCTCTTACT
 721 CAACCATTTC TGGGAAGCCC TTAGGATTCC TACAAATCAA TGATATGCTC AGCAGATACA
 781 GTTCAGTGTT ATACGCAGTG CAGTGATACG GAACACACCC ATGATGTTT AATTTTTTT
 841 TTTCTTTCCT AAAATCTAGG TGTGTTCACG GGAGTTTGTT GCCCATATGA CCGTCTTCCA
 901 TCATTCTGGT GGGGCTGCGG GGGGACCGAT AAACATGGTT ACTTTAGAAA AGCATTCTCA
 961 TGACGTATTT GCTATGTAAA AGAAGGGAAT TAGACCTCAG AAGCTTGTGA CTACCCCACT
1021 CCAGATTGCA TTTAAGTAAA GCAGCACCAT TTAGATCTGG ATAAATTTAG AGCTTATAAT
1081 ATAGGTCAGG AACAGGACGA ATTTTCTCAG TAAGGGGAGT ATATTTTGGA TCGGTGCCTT
1141 TTTTTTAGGA AGTCTGTGGA AATCCACACT ATGCTCTTAT TTAGGGAATG GAAAGAATGA
1201 GGTTAAATGA TCATTTGTCA GTTAAAACTG CTGTCTAGAT TCCTGGTGGA GAATTAAACT
1261 TACTTTTTCT TTTTCATTCA TATAAAACAT TTGAAATGAG GAAGCTGGGA TACTTTAAAA
1321 TGCCATTACT TATTTTGTTT TAATTTCCAG GTAATTCCTG AGACAGTACT GCCCCAATA
1381 GCCTTTGCAA TTACTTAAGA ATATCCAAGG TAATTCTTAC ATTCCTCAAT TCAAACGAAC
1441 CACATAATTA CAATTTTAAT AGGAACTCTA GAAAAGGGAG TCAGAATTTA TCCCAAGATA
1501 ATTACACTGG GTCCACTCTA CACTGGAATA AATATGTATA AAAAAAAATA GGAAATTCAA
1561 TGCACTGAAT TTTAAGCTGT CAAAACAAGA TTATTGAAAT ATTCTGTTAA AGGTTAAAAA
1621 TAAGTTGTAC TCTGAGTCCA GTGACCATTT GCCAAGGAGA GCCAAGTTG AGAAATTTCT
1681 ATTAAAAACA TGACTCAGAG GGAAAACTGC AGAGGCTGGC AATGAAGGAA ATGATCGGAT
1741 ATCATTCCCA ATTGGTTATG CCCAAGATCA CATGATCTGG GCACCTTTAA AAGGAAGATA
1801 TCTGGACTCA GAGGGTAATA GCATCTTGCT GAAAGCTGCA CTTCTTTCTC ACCTTGAAGA
1861 ATTCTAGAAA GCTCACAAAA TGTGTGATGC ATTTGTAGGT ACCTGGAAAC TTGTCTCCAG
1921 TGAAAACTTT GATGATTACA TGAAAGAAGT GGGTAAGGAA ATGCATTGTT GAATGGCTGG
1981 GCTTATAACT TTTTCTCTAG GAAAGAGAGG CCTATGGTTC TTTTTCACTC TGGAAGCATT
2041 GGTCTGACAT GAAATGCTGC TTTCTATACA GAGGTGATAA AAATAACAAG TGAGAATCAT
2101 TTGTTTCCAG AAACATTCTA GATGGAAGTC ACAACTAATA CTTCCTAAAG GTGAACTGAT
2161 ATGAAAAAGA GTATAAGTGG CATTGTATAG AAATGACAAG ATTTTATTTG ATTGCTAAAC
2221 TTGAGTATCT TTGGTTTACT TGGCTTTCTG CCTCTTTTTC ATTCATTCCT TTTGCATATA
2281 AAATAAGCAA TAACTTGGAA ATAAGCCTAT ATTTATTCCC TAGCATGTGA TAATTTCCAT
2341 TTGAAACTGA AAGCACTGTA TTTATCATCT TAACATAATT TTTTGAGTAA TGTATGTTAA
2401 CCAATTATTT TATTGTTTTA AAGTCAATCT GTTAAAATGT GTGGTTGTAT TATGGAAGGA
2461 AAAAATCTAA TTTCTGAAAA TGTTTCCTTA AAAGTCTTAG ATATTTGTTT GACTTAATAT
2521 TACAAGGCAT GACACAGAAT TATTGAGAAT AGAGGCTTTC AAGTTTTTGG ATTCTGCTAA
2581 GACTGCCTGT ATGTTCCCCA GATAATTACA AAGGTAAAGC AAAGGAGCAG AGAGGCGGGA
2641 ATTCAGTCAG ACAGCCCTAC CCATGCATGA TGAAGATGTA TCCATGGGTT GCAAATTAAG
2701 GAGGGATTTT TTTCACAATA TCTTTATTAG AGGTTATAAT TTAATCCCTA AATCTCAAGA
2761 CTTAACCTTC TTCTAAATCT TATAGTTATT TCTTGCTTGT TTATAACTAC TGTTTTCCAT
2821 GTTTATAGAC AAGAAGGAAA TCAGGAACAT CAATATGAGT GAGAACTAGT TTTCCAGACT
2881 TCTGACTAGT TGTAACTCAA TAAACTAATC AGTATGCACT GATATTGATA TTATAGGACT
2941 TGAGTCTATT TACCTATTTA TTTTTAGAAG CATTTTACAC TTTTAGTATT TTATTTAAAT
3001 TCTTATACCA TTGCGTTTGG GCTTCCTATA TGGTGCTAGT GGTAAAGAAC CCACCTGCCA
```

FIG. 4 (1/3) – SEQ ID NO:1

```
3061 ATTCAGGAGA TTTAAGAGAC AGAGGGTTCG ATTCCTGGGT CAGGAAGATT CCCCTAGAGG
3121 AGGGCATGGC AACCTACTTC AGTATTCTTG CCTGGAGAAT CCCATGAACA GAGGAGCCTG
3181 GTGCACTATG GTTCATAGGG TTGCAAAGAG TCAGACATGA CTGAAGAGAC TTAGCACACA
3241 TGCAGGCACC ACAGTCTTTT AAAATGATTA AGTATTGATG ATAATGAAAG ACAATAAGAT
3301 ACATTCTGAA ATTAGCTGCT CTATTTGATT ACCTTCAGTC AGCAGGTATC ATTTTCATCA
3361 GTCAAATGAA AACAGAATCA AGCAAGAGGA GAGTGTGATG TTCCTAAGCT TGGAGAATCT
3421 GGACCACACC CGATGTCTCA TGCACTCACT GTGCTGACTC ACTCCATGAA TTTGAGGTTA
3481 CATTTTGTAA CAGAGACAAG ACTTGATGAA GCAGCATATT ATCTTCCCAC CTGTCACCAC
3541 TTTCAGACAG GGGGCTAAAT CAGAGCCTTA GCATTGCTTG TTTTGTATGA TATATCGCCT
3601 CCCCACTATT CTTAAATTTT GGTATCTATA CATAGTCAAA GAAGTAGATT TGTACATGTG
3661 CATTTAAAAA GTCCAACACA CCTATGACTG TCATAAATCT CTATAAACA TGCAGTGATG
3721 GTAAGGTACT GTTTTCTATG TTAAGTTGTA AATAATTCAA CCCAAAGCTG TAACATCCCC
3781 CAAAACACAT TCATATTTTT TCTTTTTTA AAAAGAGGA GTTTGCCACT TAAGTGATTG
3841 GGAAGCAAAG TATTAATTTC TGAACTTACT AAAATAACGA TTTCTTAAAC TTTGAAATTT
3901 TCATTTGATG CCTAAGCCCT CTTTAAATTT TTCTATAATT TATTGGGAAT ACCATCACCA
3961 TTCTAAAATG GTATGAATGC AAGAAAGTT TTGCCTTTCA GAAAAGTAA TCAAGATCTT
4021 CATTTCAGAG TAATTATGAA AAGCCAAGAA AACTAGGTGT GGCAGCGAAT CCCATTAAAT
4081 GTGGTTTTG TACACCCAAA TTAAATTTTA ACTGAGTGAC TCTCTATTGG TCCCCTGAAT
4141 CCTATTAAAA GTTCTACTTT TGACTATGGA TTAGATCATT TTTGTTATTC AAGAAGCAAT
4201 GGTTGAGATT CCCAAGTATT TCATGAACTG AGTCAAATGA AGCTGGCTGC TCTCATGGTT
4261 AAGATGGACA GTTATTTTGG GAGTGCAGTG ATTTTTACGA TATGTATGTC CCAGAAAATT
4321 TAACCTTTTA CATATGCTTA TAGAAAATTA ACAATGGGTC TCCTGAAGAG TCTCATCTGA
4381 AACCCAGAGG GGGAAATTTA AGAACAGAC TTAATATCTA ATTGTGCCTT GGGTGTTCTT
4441 TAAGTATTAG CTGATTTTAC TTATTTTCAG GAGATGTTTA AATAAAGACT TTAATAATAA
4501 ACTCACTGGA GTATTTCTCC TTTAATATAC ACACTGGACT GTAGATAGGT ATATGGGCAC
4561 ACATGCGTCT GTCTAAATAC ACACACACAC ACCTGCTCTT TCTTAGATAA ATATATGAGA
4621 GAAAAACTGT ATACTTGACA TTTTTCTTTT CCCAACTATA GGCGTGGGCT TTGCTACCAG
4681 GAAAGTGGCT GGCATGGCCA AACCCACTTT GATCATCAGT TTGAATGGGG GTGTGGTCAC
4741 CATTAAATCA GAAAGCACCT TTAAAAATAC TGAGATTTCC TTCAAATTGG GCCAGGAATT
4801 TGATGAAATC ACTCCAGATG ACAGGAAAGT CAAGGTGAGA ATAAAGAAC TGGAGCAGAG
4861 TAAAAAACCT GATTTATAAA TGACTGCTGC CTATAGCAAA CCATTTGTA GAAGGAGGAA
4921 AGCCATTCCA TTATAAGCCA AAAATCTCAG ATTGCTAGAT CTGAACCATG TTACCTTTGA
4981 TATTTAGCTG GTGAATTTTC TCCCATTTAA TAAAATTGTC CTTATTACTT TAAAAATGTT
5041 TAACATAATA ATTTACTTGT CATACCCATAT ATATGTGTGT ATTTATATAT ATATATATAT
5101 ATATTATTTG AAGTAAATTG AAGTAACATA ACAATGTTAG AGAACTTTTA AAAGAGTGGG
5161 GGGAAAGGAA AAAAAAACC CCTATGATGC TATTCCACAT AAATTTATTA TCTATATTCT
5221 TTCACAGTAT TTTTTTTTCA AATGCATGTT TGTATAATAT TCTGATCATA ATATACATGT
5281 AATTTTGTAT GTTGTTTTTG GCATTCATTG TTTTATTTTG CAACATTTTC TTGTAATTTA
5341 GAATTGCTAA GAACCTCAAA ATAAGCAAAT AAAAGCACTC TATTTTTTTT CCCTCCATCA
5401 TTGTAATCAC TTTTAATTAT CCCCACAGAG CATCGTAAAC TTAGATGAAG GTGCTCTGGT
5461 ACAAGTACAA AACTGGGATG GAAAATCAAC CACCATAAAG AGAAAACTCG TGGATGATAA
5521 GATGGTGCTG GTGAGTATCT TCTCACTACT TAATTCTAGA TTTTAGTGCT AGGTCATCCC
5581 ATAATTGTTA TCCTACCTAG AGAAATAGAC AATCGCCCTT GTAGAATGAA AAGTTAGTCT
5641 ATTGGGATTA TGGTTTCACT CTGACAATTA TCCTTCTAAG CTCCGTCTAG GTATACTGTG
5701 CCCCCAGCAG TATTTTCTTA TCCCTCTCAA TGTGAACCGT ATTGTATTGT GCATTTCTAA
5761 TTATGTTTTT CACTCACCAC ATAGATGGTA AGATTCCTTG AGGCCAAGTC TTGTATCTTC
5821 TTGATCTTTG TGTCTCCCTA GTTATTACA ATATCAGGTA TATAAGAAGA GCCAAGAGGG
5881 AATATCTTTT GATGAACATT TTTTCCTGCT CAACATTGAA GGAGACAATA AATAAATAAA
5941 ACATAAGTTG TTTAGTCCTG AGGATTTTAC CAATATTTTG CTTTTGTGCC TAGGAATGTG
6001 TCATGAATGG TGTCACTGCC ACCAGAGTTT ATGAGAGAGC ATAAGCCAAG GGATATTGAA
6061 ATGGATGACG TTTGCATCGA ACTCCATGAC TTTCTGCTGG ATACGTTGTC CAAACATATA
6121 TTGTTATTTT CCACTAATAA GCAAGAAACT GATTTTCTTC CAGACTGATT TTGATATGGT
6181 TATGTTGGTT AAATAAAACT TTTTAGATTT ATAAGGCTAT GTAATCATTT ATTCATTATG
```

FIG. 4 (2/3) – SEQ ID NO:1

```
6241 TTTAACAATT TCTTACTCAT AATTTAGTGA TGGAAATATA AAATTGTATT ATTGCTTTGT
6301 TTCCAGTATA ATATGATTTG TAAATAATA ATCCAAGGTG AAAAAAATAT GAATTTCCCA
6361 TAGTCTTAGG TAGAAAATGA TAAATATATA CTATTACTGA ATATGAAGTC CTTCTTTACC
6421 ATAGCTACAG TCAAACAACA CCCTCTCAGG GACCTAAGAT AGATTTAAGT GTAGTGAAAT
6481 TGTCCACAGT CGGCTGGCCC GTGTTGTCAT TTCACAAAAA TCTGTCCTAG AGCATCAAGA
6541 CATAGAGGTG GAGTAGCAAC AAAGAGTGTA GAAAAGATT TCTGGGCTAT AAATTTTAAC
6601 CTGAAAAATT ATTAGTAAAC CAAGGTATCC CTGGAATCTG TCTAGAATTA AGTCCAAATC
6661 ATCACATGTT ACATTTATTC CAGAAAAGAC ATGACAGGCT TGTAATGAGT TATGATGTAA
6721 ATGTTCTTGT AGTCATTTCC AAATTTTCT TTTTTTCTTA CCAGTGGATT TTTTTAAAA
6781 AAAATAGATA TTGAATATGT CCTGGAATTT TTATGCAAA TAAAATTTCC CTGGAATTTC
6841 AATATATAAA ACAAACAAAA ATGATAATAA AGCCCGTAAG GGTGTGTTTT CATTTGTGTG
6901 TGAGAGAAAG AGAGAGAAAA TTTGTTTCTT CTGCACTCTG TGGAAATTTG AGGCATCTCT
6961 ATAGATCCTT GGAGTTCCAT GTACATAGAC TGAAATTTCC CTATCACATA CTTAGCTCTT
7021 ATGGGAAGCC AAAATCTTTT AAAGTGTGTC CTGCAATTGA TACATTCTGT TTGTGATGCT
7081 TCCTTTAAAA ATAAGTTTAT TAGAGACTTC CTGGTGGCTC AGATGGTAAA AGAATCCACC
7141 TGCAGTGCAG GAGACCCCAG TTTGATCCCT GGGTTGGGAA GATCCCCTGG AGGAGGGCAT
7201 GGCAACCCAC TCCAGTATTC TTGCCTGGAG AATCCTGTGG ACAGAGGAGC CTTCTGGGCT
7261 ACAGTCCGTG GGGTTGCAAA GAGTTAAACA CAAGAGAGTG AGTGATTAAG ATTCCATGCT
7321 TCCACTGCTG GAGGAGTAGT TCAATCTCTG GTCAAGTAAC TAAGTTTCCA CATTCCACAC
7381 AGCATGGAAA AAAAGAAAAC ATTTATTGTT TTCTGAATAT AGTCCATAGG GTGGCAAAGA
7441 GTTCGAAACA ACTGAAGCAG CTTAGCATGC ACACATGCAC CATATGCATA GGTGGCGTTA
7501 GCGATGAAAA ACCCCGCTGC CAATGTGGGA GACATAAGAG ATGCAGGTTT GATCCCTGGG
7561 TCAGGAAGAT CCCCTGGAGG AGGGCATGGC AACTCACTCC AGTATCCTTG CCTGGAGAAT
7621 CCCATGGACA GAGGAGCCTG GTGGCCTATA GTCCATAGGA TCACAAAGAG TCAGACACAA
7681 CTGAAGCGAC TTAGCACACA CAGACACACA CAGACACACA CACACACACA CTATATGCAT
7741 AACACCAAGA TACAGAGAAG CCAGAAGAGG TAAATTAAGT TTCTGATCAT AATAATTTAC
7801 TTTACAAAAG CAGAGAGTTA AACTCTCACT TTGAAATTAC TTAAGAATGG AGAATTCAAA
7861 GAGAGGTTTG TAGGAATTGT TTAGAAAAAT TCTTGGTAAA TCAATATGTA TTAAACACTT
7921 ACCATGGTCC ATGCAGAGAC ATTACTTTAC CAACAAAGGT CTGTCTAGTC AAGGCTATGG
7981 TTTTTCCTGT GGTCATGTAT GGATATGAGA GTTGGACTGT GAAGAAGGCT G
```

FIG. 4 (3/3) – SEQ ID NO:1

SEQUENCE LISTING

```
<160> NUMBER OF SEQ ID NOS: 9

<210> SEQ ID NO 1
<211> LENGTH: 8031
<212> TYPE: DNA
<213> ORGANISM: Bos taurus

<400> SEQUENCE: 1
gcagccaaaa atggagaagc tctatacagt cagcaaaaac aagactggga gctgactgtg      60
gctcagatca tgagttcctt attgccaaat tcagacttaa attgaagaaa gcagggaaaa     120
ccactagacc attcaggcat gacctaaatc aaaacaacaa caacatgtca ttatattaat     180
actttgtcca aacacatgga acatataata ccaaaagtga accctaaggt aatatatgga     240
ctttgagtga ttataatata ccaatatagg ttcattctta gtaaaaatta ccattctggt     300
gaatgatatt gataatgggg gaggctatcc atatgcggga acagggagta catgagaaat     360
ctctgtactt tcctctcaat tttgttataa acctgaaact tctctaaaaa attatcataa     420
aagcaaaaca aactaaaaac aaaagccatt tattagttta gaacatgaag ttatccctgt     480
atgaaacttg atcattttta ttttcttgtt cgatgaattc ataatagtaa gcctaccctg     540
aatggtacat cacccacagt ctataatatg tctatgcaac agttcagact gaatgatcat     600
tatcactgtg ccgttaacat atgcaaccat taaaagttac tattgtaaca caactttacc     660 cgttttttctt agcaaattttc atgcctacag aaaatctgtc ctttacggaa tcctcttact    720
caaccatttc tgggaagccc ttaggattcc tacaaatcaa tgatatgctc agcagataca     780
gttcagtgtt atacgcagtg cagtgatacg gaacacaccc catgatgttt taattttttt     840
```

```
tttctttcct aaaatctagg tgtgttcacg ggagtttgtt gcccatatga ccgtcttcca    900
tcattctggt ggggctgcgg ggggaccgat aaacatggtt actttagaaa agcattctca    960
tgacgtattt gctatgtaaa agaagggaat tagacctcag aagcttgtga ctacccact    1020
ccagattgca tttaagtaaa gcagcaccat ttagatctgg ataaatttag agcttataat    1080
ataggtcagg aacaggacga attttctcag taaggggagt atattttgga tcggtgcctt    1140
tttttttagga agtctgtgga aatccacact atgctcttat ttagggaatg gaaagaatga    1200
ggttaaatga tcatttgtca gttaaaactg ctgtctagat tcctggtgga gaattaaact    1260
tacttttct ttttcattca tataaaacat ttgaaatgag gaagctggga tacttaaaa    1320
tgccattact tattttgttt taatttccag gtaattcctg agacagtact gcccccaata    1380
gcctttgcaa ttacttaaga atatccaagg taattcttac attcctcaat tcaaacgaac    1440
cacataatta caattttaat aggaactcta gaaaagggag tcagaattta tcccaagata    1500
attacactgg gtccactcta cactggaata aatatgtata aaaaaaaata ggaaattcaa    1560
tgcactgaat tttaagctgt caaaacaaga ttattgaaat attctgttaa aggttaaaaa    1620
taagttgtac tctgagtcca gtgaccattt gccaaggaga gccaaagttg agaaatttct    1680
attaaaaaca tgactcagag ggaaaactgc agaggctggc aatgaaggaa atgatcggat    1740
atcattccca attggttatg cccaagatca catgatctgg gcaccttaa aaggaagata    1800
tctggactca gagggtaata gcatcttgct gaaagctgca cttctttctc accttgaaga    1860
attctagaaa gctcacaaaa tgtgtgatgc atttgtaggt acctggaaac ttgtctccag    1920
tgaaaacttt gatgattaca tgaaagaagt gggtaaggaa atgcattgtt gaatggctgg    1980
gcttataact ttttctctag gaagagagg cctatggttc tttttcactc tggaagcatt    2040
ggtctgacat gaaatgctgc tttctataca gaggtgataa aaataacaag tgagaatcat    2100
ttgtttccag aaacattcta gatggaagtc acaactaata cttcctaaag gtgaactgat    2160
atgaaaaaga gtataagtgg cattgtatag aaatgacaag attttatttg attgctaaac    2220
ttgagtatct ttggtttact tggctttctg cctctttttc attcattcct tttgcatata    2280
aaataagcaa taacttggaa ataagcctat atttattccc tagcatgtga taatttccat    2340
ttgaaactga agcactgta tttatcatct taacataatt ttttgagtaa tgtatgttaa    2400
ccaattattt tattgtttta aagtcaatct gttaaaatgt gtggttgtat tatggaagga    2460
aaaaatctaa tttctgaaaa tgtttcctta aaagtcttag atatttgttt gacttaatat    2520
tacaaggcat gacacagaat tattgagaat agaggctttc aagttttttgg attctgctaa    2580
gactgcctgt atgttcccca gataattaca aaggtaaagc aaaggagcag agaggcggga    2640
attcagtcag acagccctac ccatgcatga tgaagatgta tccatgggtt gcaaattaag    2700
gagggatttt tttcacaata tcttattag aggttataat ttaatcccta aatctcaaga    2760
cttaaccttc ttctaaatct tatagttatt tcttgcttgt ttataactac tgttttccat    2820
gtttatagac aagaaggaaa tcaggaacat caatatgagt gagaactagt tttccagact    2880
tctgactagt tgtaactcaa taaactaatc agtatgcact gatattgata ttataggact    2940
tgagtctatt tacctatta tttttagaag cattttacac ttttagtatt ttatttaaat    3000
tcttatacca ttgcgtttgg gcttcctata tggtgctagt ggtaaagaac ccacctgcca    3060
attcaggaga tttaagagac agagggttcg attcctgggt caggaagatt cccctagagg    3120
agggcatggc aacctacttc agtattcttg cctggagaat cccatgaaca gaggagcctg    3180
gtgcactatg gttcataggg ttgcaaagag tcagacatga ctgaagagac ttagcacaca    3240
```

```
tgcaggcacc acagtctttt aaaatgatta agtattgatg ataatgaaag acaataagat    3300
acattctgaa attagctgct ctatttgatt accttcagtc agcaggtatc attttcatca    3360
gtcaaatgaa aacagaatca agcaaggaga gagtgtgatg ttcctaagct tggagaatct    3420
ggaccacacc cgatgtctca tgcactcact gtgctgactc actccatgaa tttgaggtta    3480
cattttgtaa cagagacaag acttgatgaa gcagcatatt atcttcccac ctgtcaccac    3540
tttcagacag ggggctaaat cagagcctta gcattgcttg ttttgtatga tatatcgcct    3600
ccccactatt cttaaatttt ggtatctata catagtcaaa gaagtagatt tgtacatgtg    3660
catttaaaaa gtccaacaca cctatgactg tcataaatct ctataaaaca tgcagtgatg    3720
gtaaggtact gttttctatg ttaagttgta aataattcaa cccaaagctg taacatcccc    3780
caaaacacat tcatattttt tcttttttta aaaagagga gtttgccact taagtgattg    3840
ggaagcaaag tattaatttc tgaacttact aaaataacga tttcttaaac tttgaaattt    3900
tcatttgatg cctaagccct ctttaaattt ttctataatt tattgggaat accatcacca    3960
ttctaaaatg gtatgaatgc aagaaaagtt ttgccttcca gaaaagtaa tcaagatctt    4020
catttcagag taattatgaa aagccaagaa aactaggtgt ggcagcgaat cccattaaat    4080
gtggttttg tacacccaaa ttaaattta actgagtgac tctctattgg tcccctgaat    4140
cctattaaaa gttctacttt tgactatgga ttagatcatt tttgttattc aagaagcaat    4200
ggttgagatt cccaagtatt tcatgaactg agtcaaatga agctggctgc tctcatggtt    4260
aagatggaca gttattttgg gagtgcagtg attttacga tatgtatgtc ccagaaaatt    4320
taaccttta catatgctta tagaaaatta acaatgggtc tcctgaagag tctcatctga    4380
aacccagagg gggaaattta agaacagac ttaatatcta attgtgcctt gggtgttctt    4440
taagtattag ctgattttac ttattttcag gagatgttta aataaagact ttaataataa    4500
actcactgga gtatttctcc tttaatatac acactggact gtagataggt atatgggcac    4560
acatgcgtct gtctaaatac acacacacac acctgctctt tcttagataa atatatgaga    4620
gaaaaactgt atacttgaca ttttttcttt ccccaactata ggcgtgggct ttgctaccag    4680
gaaagtggct ggcatggcca aacccacttt gatcatcagt ttgaatgggg gtgtggtcac    4740
cattaaatca gaaagcacct ttaaaaatac tgagatttcc ttcaaattgg gccaggaatt    4800
tgatgaaatc actccagatg acaggaaagt caaggtgaga aataaagaac tggagcagag    4860
taaaaaacct gatttataaa tgactgctgc ctatagcaaa ccattttgta gaaggaggaa    4920
agccattcca ttataagcca aaaatctcag attgctagat ctgaaccatg ttacctttga    4980
tatttagctg gtgaattttc tcccatttaa taaaattgtc cttattactt taaaaatgtt    5040
taacataata atttacttgt cataccatat atatgtgtgt atttatatat atatatatat    5100
atattttg aagtaaattg aagtaacata acaatgttag agaactttta aaagagtggg    5160
gggaaggaa aaaaaaacc cctatgatgc tattccacat aaatttatta tctatattct    5220
ttcacagtat ttttttttca aatgcatgtt tgtataatat tctgatcata atatacatgt    5280
aattttgtat gttgttttg gcattcattg ttttattttg caacatttc ttgtaattta    5340
gaattgctaa gaacctcaaa ataagcaaat aaaagcactc tatttttttt ccctccatca    5400
ttgtaatcac tttaattat ccccacagag catcgtaaac ttagatgaag gtgctctggt    5460
acaagtacaa aactgggatg gaaaatcaac caccataaag agaaaactcg tggatgataa    5520
gatggtgctg gtgagtatct tctcactact taattctaga ttttagtgct aggtcatccc    5580
ataattgtta tcctacctag agaaatagac aatcgccctt gtagaatgaa aagttagtct    5640
```

```
attgggatta tggtttcact ctgacaatta tccttctaag ctccgtctag gtatactgtg    5700 ccccccagcag tatttctta tccctctcaa tgtgaaccgt attgtattgt gcatttctaa    5760
ttatgttttt cactcaccac atagatggta agattccttg aggccaagtc ttgtatcttc    5820
ttgatctttg tgtctcccta gtttattaca atatcaggta tataagaaga gccaagaggg    5880
aatatctttt gatgaacatt ttttcctgct caacattgaa ggagacaata aataaataaa    5940
acataagttg tttagtcctg aggattttac caatattttg cttttgtgcc taggaatgtg    6000
tcatgaatgg tgtcactgcc accagagttt atgagagagc ataagccaag ggatattgaa    6060
atggatgacg tttgcatcga actccatgac tttctgctgg atacgttgtc caaacatata    6120
ttgttatttt ccactaataa gcaagaaact gattttcttc cagactgatt ttgatatggt    6180
tatgttggtt aaataaaact ttttagattt ataaggctat gtaatcattt attcattatg    6240
tttaacaatt tcttactcat aatttagtga tggaaatata aaattgtatt attgctttgt    6300
ttccagtata atatgatttg taaaataata atccaaggtg aaaaaaatat gaatttccca    6360
tagtcttagg tagaaaatga taaatatata ctattactga atatgaagtc cttctttacc    6420
atagctacag tcaaacaaca ccctctcagg gacctaagat agatttaagt gtagtgaaat    6480
tgtccacagt cggctggccc gtgttgtcat ttcacaaaaa tctgtcctag agcatcaaga    6540
catagaggtg gagtagcaac aaagagtgta gaaaaagatt tctgggctat aaattttaac    6600
ctgaaaaatt attagtaaac caaggtatcc ctggaatctg tctagaatta agtccaaatc    6660
atcacatgtt acatttattc cagaaaagac atgacaggct tgtaatgagt tatgatgtaa    6720
atgttcttgt agtcatttcc aaattttttct tttttttctta ccagtggatt ttttttaaaa    6780
aaaatagata ttgaatatgt cctggaattt tttatgcaaa taaaatttcc ctggaatttc    6840
aatatataaa acaaacaaaa atgataataa agcccgtaag ggtgtgtttt catttgtgtg    6900
tgagagaaag agagagaaaa tttgtttctt ctgcactctg tggaaatttg aggcatctct    6960
atagatcctt ggagttccat gtacatagac tgaaatttcc ctatcacata cttagctctt    7020
atgggaagcc aaaatctttt aaagtgtgtc ctgcaattga tacattctgt ttgtgatgct    7080 tccttttaaaa ataagtttat tagagacttc ctggtggctc agatggtaaa agaatccacc    7140
tgcagtgcag gagaccccag tttgatccct gggttgggaa gatcccctgg aggagggcat    7200
ggcaacccac tccagtattc ttgcctggag aatcctgtgg acagaggagc cttctgggct    7260
acagtccgtg gggttgcaaa gagttaaaca caagagagtg agtgattaag attccatgct    7320
tccactgctg gaggagtagt tcaatctctg gtcaagtaac taagtttcca cattccacac    7380
agcatggaaa aaaagaaaac atttattgtt ttctgaatat agtccatagg gtggcaaaga    7440
gttcgaaaca actgaagcag cttagcatgc acacatgcac catatgcata ggtggcgtta    7500
gcgatgaaaa accccgctgc caatgtggga gacataagag atgcaggttt gatccctggg    7560
tcaggaagat cccctggagg agggcatggc aactcactcc agtatccttg cctggagaat    7620
cccatggaca gaggagcctg gtggcctata gtccatagga tcacaaagag tcagacacaa    7680
ctgaagcgac ttagcacaca cagacacaca cagacacaca cacacacaca ctatatgcat    7740
aacaccaaga tacagagaag ccagaagagg taaattaagt ttctgatcat aataatttac    7800
tttacaaaag cagagagtta aactctcact ttgaaattac ttaagaatgg agaattcaaa    7860
gagaggtttg taggaattgt ttagaaaaat tcttggtaaa tcaatatgta ttaaacactt    7920
accatggtcc atgcagagac attactttac caacaaaggt ctgtctagtc aaggctatgg    7980
tttttcctgt ggtcatgtat ggatatgaga gttggactgt gaagaaggct g             8031
```

-continued

```
<210> SEQ ID NO 2
<211> LENGTH: 27
<212> TYPE: DNA
<213> ORGANISM: Artificial Sequence
<220> FEATURE:
<223> OTHER INFORMATION: synthetic primer

<400> SEQUENCE: 2
tcgtaaactt agatgaaggt gctctgg                                              27

<210> SEQ ID NO 3
<211> LENGTH: 25
<212> TYPE: DNA
<213> ORGANISM: Artificial Sequence
<220> FEATURE:
<223> OTHER INFORMATION: synthetic primer

<400> SEQUENCE: 3
acgtatccag cagaaagtca tggag                                                25

<210> SEQ ID NO 4
<211> LENGTH: 24
<212> TYPE: DNA
<213> ORGANISM: Artificial Sequence
<220> FEATURE:
<223> OTHER INFORMATION: synthetic primer

<400> SEQUENCE: 4
atatagtcca tagggtggca aaga                                                 24

<210> SEQ ID NO 5
<211> LENGTH: 25
<212> TYPE: DNA
<213> ORGANISM: Artificial Sequence
<220> FEATURE:
<223> OTHER INFORMATION: synthetic primer

<400> SEQUENCE: 5
aacctctctt tgaattctcc attct                                                25

<210> SEQ ID NO 6
<211> LENGTH: 15
<212> TYPE: DNA
<213> ORGANISM: Bos taurus

<400> SEQUENCE: 6
aaaccccgct gccaa                                                           15

<210> SEQ ID NO 7
<211> LENGTH: 15
<212> TYPE: DNA
<213> ORGANISM: Bos taurus

<400> SEQUENCE: 7 aaaccccct gccaa                                                            15

<210> SEQ ID NO 8
<211> LENGTH: 36
<212> TYPE: DNA
<213> ORGANISM: Bos taurus

<400> SEQUENCE: 8
gcacacacag acacacacag acacacacac acacac                                    36
```

```
<210> SEQ ID NO 9
<211> LENGTH: 36
<212> TYPE: DNA
<213> ORGANISM: Bos taurus

<400> SEQUENCE: 9
gcacacacag acacacacac acacacacac acacac                                    36
```

POLYMORPHISMS IN FATTY ACID BINDING PROTEIN 4 ("FABP4") GENE AND THEIR ASSOCIATIONS WITH MEASURES OF MARBLING AND SUBCUTANEOUS FAT DEPTH IN BEEF CATTLE

INCORPORATION BY REFERENCE

This application claims benefit of U.S. provisional patent application Ser. No. 60/690,408 filed Jun. 13, 2005.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention relates to the identification of single nucleotide polymorphisms (SNPs) within the bovine genes encoding fatty acid binding protein 4 ("FABP4") and their associations with economically relevant traits in beef production. The invention further relates to methods and systems, including network-based processes, to manage the SNP data and other data relating to specific animals and herds of animals, veterinarian care, diagnostic and quality control data and management of livestock which, based on genotyping, have predictable meat quality traits, husbandry conditions, animal welfare, food safety information, audit of existing processes and data from field locations.

BACKGROUND OF THE INVENTION

Significant improvements in animal performance, efficiency and carcass and meat quality have been made over the years through the application of standard animal breeding and selection techniques. However, such classical animal breeding techniques require several years of genetic evaluation of performance records on individual animals and their relatives and are therefore very expensive. Other efforts have been made to improve productivity and quality through the application of such management practices as the use of feed additives, animal hormonal implants and chemotherapeutics. However, there is significant political and regulatory resistance to the introduction and use of such methodologies. Such methodologies are also non-inheritable and need to be applied differently in every production system.

There is a need for methods that allow relatively easy and more efficient selection and breeding of farm animals with an advantage for an inheritable trait of circulating leptin levels, feed intake, growth rate, body weight, carcass merit and carcass composition. The economic significance of the use of genetic markers that are associated with specific economically important traits (especially traits with low heritability) in livestock through marker-assisted selection cannot therefore be over-emphasized.

The physiological regulation of intake, growth and energy partitioning in animals is under the control of multiple genes, which may be important candidates for unraveling the genetic variation in economically relevant traits (ERT) in beef production. Polymorphisms in these candidate genes that show association with specific ERT are useful quantitative trait nucleotides for marker-assisted selection. In the present study, associations between single nucleotide polymorphisms (SNPs) in the fatty acid binding protein 4 ("FABP4") gene with marbling and subcutaneous fat depth have been found.

Fatty acid binding proteins are a family of small, highly conserved, cytoplasmic proteins that bind long-chain fatty acids and other hydrophobic ligands (Kaikaus et al. 1990. Experientia, 46: 617-630). Their major functions include fatty acid uptake, transport, and metabolism. So far, nine distinct members have been identified in this gene family (Damcott et al. 2004. Metabolism, 53: 303-309), including adipocyte fatty acid binding protein or fatty acid binding protein 4 ("FABP4"). FABP4 plays a major role in the regulation of lipid and glucose homeostasis through its interaction with perioxisome proliferator-activated receptors (PPARs), located in the cell nucleus Specifically; the FABP4/fatty acid complex activates the PPAR-$\gamma$ isoform, which in turn, regulates transcription of FABP4 (Damcott et al. 2004. Metabolism, 53: 303-309). In addition, FABP4 appears to be involved in lipid hydrolysis and intracellular fatty acid trafficking through direct interaction and binding to hormone-sensitive lipase (Shen et al. 1999. Proc Natl Acad Sci U S A, 96: 5528-5532), which is a primary enzyme involved in lipid catabolism (Tansey et al. 2003. J Biol Chem. 278: 8401-8406). Recently, FABP4 and FABP5 were proposed as potential candidate genes for obesity as they are located within a quantitative trait loci (QTL) region for serum leptin levels in mice (Ogino et al. 2003. Mamm Genome, 14: 839-844). Leptin, a 16-kDa protein secreted from white adipocytes, is involved in the regulation of food intake, energy expenditure, and whole-body energy balance (Jiang and Gibson 1999. Mamm Genome, 10: 191-193). All these factors indicate that FABP4 may play an important role in lipid metabolism and homeostasis in adipocytes.

It remains advantageous to provide further SNPs that may more accurately predict the meat quality phenotype of an animal and also a business method that provides for increased production efficiencies in livestock cattle, as well as providing access to various records of the animals and allows comparisons with expected or desired goals with regard to the quality and quantity of animals produced.

Citation or identification of any document in this application is not an admission that such document is available as prior art to the present invention.

SUMMARY OF THE INVENTION

The present invention relates to the identification of single nucleotide polymorphisms (SNPs) within the bovine genes encoding fatty acid binding protein 4 ("FABP4") and their associations with economically relevant traits in beef production.

The invention encompasses a method for sub-grouping animals according to genotype wherein the animals of each sub-group have a similar polymorphism in a FABP4 gene which may comprise determining the genotype of each animal to be sub-grouped by determining the presence of a single nucleotide polymorphism in the FABP4 gene, and segregating individual animals into sub-groups wherein each animal in a sub-group has a similar polymorphism in the FABP4 gene.

The invention also encompasses a method for sub-grouping animals according to genotype wherein the animals of each sub-group have a similar genotype in the FABP4 gene which may comprise determining the genotype of each animal to be sub-grouped by determining the presence of a single nucleotide polymorphism(s) of interest in the FABP4 gene, and segregating individual animals into sub-groups depending on whether the animals have, or do not have, the single nucleotide polymorphism(s) of interest in the FABP4 gene.

The single nucleotide polymorphism(s) of interest may be selected from the group consisting of a G to C substitution at the 7516 nucleotide position of the FABP4 gene and a G to C substitution at position 7713 of the FABP4 gene.

The invention further relates to a method for sub-grouping animals according to genotype wherein the animals of each sub-group have a similar genotype in the FABP4 gene which may comprise determining the genotype of each animal to be subgrouped by determining the presence of any one of the above SNPs, and segregating individual animals into sub-groups depending on whether the animals have, or do not have, any one of the above SNPs in the FABP4 gene.

The invention also relates to method for identifying an animal having a desirable phenotype as compared to the general population of animals of that species, which may comprise determining the presence of a single nucleotide polymorphism in the FABP gene of the animal, wherein the presence of the SNP is indicative of a desirable phenotype.

In an advantageous embodiment, the animal may be a bovine. In another advantageous embodiment, the FABP4 gene may be a bovine FABP gene.

The invention also encompasses computer-assisted methods and systems for improving the production efficiency for livestock having marketable tender meat using multiple data, and in particular the genotype of the animals as it relates to FABP4 SNPs. Methods of the invention encompass obtaining a genetic sample from each animal in a herd of livestock, determining the genotype of each animal with respect to specific quality traits as defined by a panel of at least two single polynucleotide polymorphisms (SNPs), grouping animals with like genotypes, and optionally, further sub-grouping animals based on like phenotypes. Methods of the invention may also encompass obtaining and maintaining data relating to the animals or to herds, their husbandry conditions, health and veterinary care and condition, genetic history or parentage, and providing this data to others through systems that are web-based, contained in a database, or attached to the animal itself such as by an implanted microchip. An advantageous aspect of the present invention, therefore, is directed to a computer system and computer-assisted methods for tracking quality traits for livestock possessing specific genetic predispositions.

The present invention advantageously encompasses computer-assisted methods and systems for acquiring genetic data, particularly genetic data as defined by the absence or presence of a SNP within the FABP4 gene related to meat quality traits of the breed of animal and associating those data with other data about the animal or its herd, and maintaining those data in ways that are accessible. Another aspect of the invention encompasses a computer-assisted method for predicting which livestock animals possess a biological difference in meat quality, and which may include the steps of using a computer system, e.g., a programmed computer comprising a processor, a data storage system, an input device and an output device, the steps of: (a) inputting into the programmed computer through the input device data that includes a genotype of an animal as it relates to any one of the FABP SNPs described herein, (b) correlating meat quality predicted by the FABP4 genotype using the processor and the data storage system and (c) outputting to the output device the meat quality correlated to the FABP4 genotype, thereby predicting which livestock animals possess a particular meat quality.

Yet another aspect of the invention relates to a method of doing business for managing livestock comprising providing to a user computer system for managing livestock comprising physical characteristics and genotypes corresponding to one or more animals or a computer readable media for managing livestock comprising physical characteristics and genotypes corresponding to one or more animals or physical characteristics and genotypes corresponding to one or more animals, wherein a physical characteristic intake, growth or carcass merit in beef cattle and the genotype is a FABP4 genotype.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings, in which:

FIG. 2 depicts two G/C substitutions detected at positions 7516 (SEQ ID NOS: 6 AND 7, respectively, in order of appearance) and 7713 (SEQ ID NOS: 8 AND 9, respectively, in order of appearance) in the bovine FABP4 gene.

FIG. 4 depicts SEQ ID NO:1 (reverse complement of GenBank Accession No. AAFC01136716, Bos taurus Cont136721, whole genome shotgun sequence).

DETAILED DESCRIPTION

Figure 1:
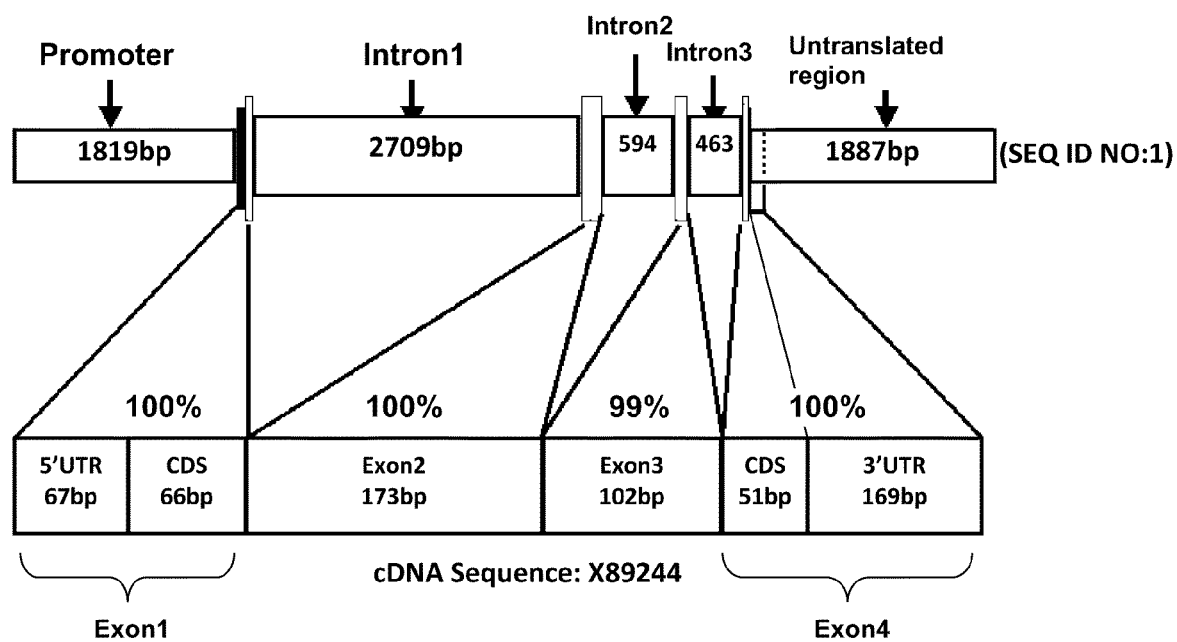
FIG. 1 depicts the sequence alignment between cDNA and genomic DNA to determine the genomic organization of the bovine FABP4 gene.

The practice of the present invention will employ, unless otherwise indicated, conventional techniques of molecular biology, microbiology, recombinant DNA technology, and immunology, which are within the skill of the art. Such techniques are explained fully in the literature. See, e.g., Sambrook et al. (2001) Molecular Cloning: A Laboratory Manual, 3rd ed., Cold Spring Harbor Press; DNA Cloning, Vols. I and II (D. N. Glover ed. 1985); Oligonucleotide Synthesis (M. J. Gait ed. 1984); Nucleic Acid Hybridization (B. D. Hames & S. J. Higgins eds. 1984); Animal Cell Culture (R. K. Freshney ed. 1986); Immobilized Cells and Enzymes (IRL press, 1986); Perbal, B., A Practical Guide to Molecular Cloning (1984); the series, Methods In Enzymology (S. Colowick and N. Kaplan eds., Academic Press, Inc.); and Handbook of Experimental Immunology, Vols. I-IV (D. M. Weir and C. C. Blackwell eds., 1986, Blackwell Scientific Publications).

Before describing the present invention in detail, it is to be understood that this invention is not limited to particular DNA, polypeptide sequences or process parameters as such may, of course, vary. It is also to be understood that the terminology used herein is for the purpose of describing particular embodiments of the invention only, and is not intended to be limiting.

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

In describing the present invention, the following terms will be employed and are intended to be defined as indicated below.

The term "cow" or "cattle" is used generally to refer to an animal of bovine origin of any age. Interchangeable terms include "bovine", "calf", "steer", "bull", "heifer" and the like. It also includes an individual animal in all stages of development, including embryonic and fetal stages. The animals as referred to herein may also include individuals or groups of individuals that are raised for other than food production such as, but not limited to, transgenic animals for the production of biopharmaceuticals including antibodies and other proteins or protein products.

By the term "complementarity" or "complementary" is meant, for the purposes of the specification or claims, a sufficient number in the oligonucleotide of complementary base pairs in its sequence to interact specifically (hybridize) with a target nucleic acid sequence of the gene polymorphism to be amplified or detected. As known to those skilled in the art, a very high degree of complementarity is needed for specificity and sensitivity involving hybridization, although it need not be 100%. Thus, for example, an oligonucleotide that is identical in nucleotide sequence to an oligonucleotide disclosed herein, except for one base change or substitution, may function equivalently to the disclosed oligonucleotides. A "complementary DNA" or "cDNA" gene includes recombinant genes synthesized by reverse transcription of messenger RNA ("mRNA").

A "cyclic polymerase-mediated reaction" refers to a biochemical reaction in which a template molecule or a population of template molecules is periodically and repeatedly copied to create a complementary template molecule or complementary template molecules, thereby increasing the number of the template molecules over time.

By the term "detectable moiety" is meant, for the purposes of the specification or claims, a label molecule (isotopic or non-isotopic) which is incorporated indirectly or directly into an oligonucleotide, wherein the label molecule facilitates the detection of the oligonucleotide in which it is incorporated, for example when the oligonucleotide is hybridized to amplified gene polymorphic sequences. Thus, "detectable moiety" is used synonymously with "label molecule". Synthesis of oligonucleotides can be accomplished by any one of several methods known to those skilled in the art. Label molecules, known to those skilled in the art as being useful for detection, include chemiluminescent, fluorescent or luminescent molecules. Various fluorescent molecules are known in the art which are suitable for use to label a nucleic acid for the method of the present invention. The protocol for such incorporation may vary depending upon the fluorescent molecule used. Such protocols are known in the art for the respective fluorescent molecule. "DNA amplification" as used herein refers to any process that increases the number of copies of a specific DNA sequence by enzymatically amplifying the nucleic acid sequence. A variety of processes are known. One of the most commonly used is the polymerase chain reaction (PCR) process of Mullis as described in U.S. Pat. Nos. 4,683,195 and 4,683,202. Methods, devices and reagents as described in U.S. Patent Nos. 6,951,726; 6,927,024; 6,924,127; 6,893,863; 6,887,664; 6,881,559; 6,855,522; 6,855,521; 6,849,430; 6,849,404; 6,846,631; 6,844,158; 6,844,155; 6,818,437; 6,818,402; 6,794,177; 6,794,133; 6,790,952; 6,783,940; 6,773,901; 6,770,440; 6,767,724; 6,750,022; 6,744,789; 6,733,999; 6,733,972; 6,703,236; 6,699,713; 6,696,277; 6,664,080; 6,664,064; 6,664,044; RE38,352; 6,650,719; 6,645,758; 6,645,720; 6,642,000; 6,638,716; 6,632,653; 6,617,107; 6,613,560; 6,610,487; 6,596,492; 6,586,250; 6,586,233; 6,569,678; 6,569,627; 6,566,103; 6,566,067; 6,566,052; 6,558,929; 6,558,909; 6,551,783; 6,544,782; 6,537,752; 6,524,830; 6,518,020; 6,514,750; 6,514,706; 6,503,750; 6,503,705; 6,493,640; 6,492,114; 6,485,907; 6,485,903; 6,482,588; 6,475,729; 6,468,743; 6,465,638; 6,465,637; 6,465,171; 6,448,014; 6,432,646; 6,428,987; 6,426,215; 6,423,499; 6,410,223; 6,403,341; 6,399,320; 6,395,518; 6,391,559; 6,383,755; 6,379,932; 6,372,484; 6,368,834; 6,365,375; 6,358,680; 6,355,422; 6,348,336; 6,346,384; 6,319,673; 6,316,195; 6,316,192; 6,312,930; 6,309,840; 6,309,837; 6,303,343; 6,300,073; 6,300,072; 6,287,781; 6,284,455; 6,277,605; 6,270,977; 6,270,966; 6,268,153; 6,268,143; D445,907; 6,261,431; 6,258,570; 6,258,567; 6,258,537; 6,258,529; 6,251,607; 6,248,567; 6,235,468; 6,232,079; 6,225,093; 6,221,595; D441,091; 6,218,153; 6,207,425; 6,183,999; 6,183,963; 6,180,372; 6,180,349; 6,174,670; 6,153,412; 6,146,834; 6,143,496; 6,140,613; 6,140,110; 6,103,468; 6,087,097; 6,072,369; 6,068,974; 6,063,563; 6,048,688; 6,046,039; 6,037,129; 6,033,854; 6,031,960; 6,017,699; 6,015,664; 6,015,534; 6,004,747; 6,001,612; 6,001,572; 5,985,619; 5,976,842; 5,972,602; 5,968,730; 5,958,686; 5,955,274; 5,952,200; 5,936,968; 5,909,468; 5,905,732; 5,888,740; 5,883,924; 5,876,978; 5,876,977; 5,874,221; 5,869,318; 5,863,772; 5,863,731; 5,861,251; 5,861,245; 5,858,725;

5,858,718; 5,856,086; 5,853,991; 5,849,497; 5,837,468; 5,830,663; 5,827,695; 5,827,661; 5,827,657; 5,824,516; 5,824,479; 5,817,797; 5,814,489; 5,814,453; 5,811,296; 5,804,383; 5,800,997; 5,780,271; 5,780,222; 5,776,686; 5,774,497; 5,766,889; 5,759,822; 5,750,347; 5,747,251; 5,741,656; 5,716,784; 5,712,125; 5,712,090; 5,710,381; 5,705,627; 5,702,884; 5,693,467; 5,691,146; 5,681,741; 5,674,717; 5,665,572; 5,665,539; 5,656,493; 5,656,461; 5,654,144; 5,652,102; 5,650,268; 5,643,765; 5,639,871; 5,639,611; 5,639,606; 5,631,128; 5,629,178; 5,627,054; 5,618,703; 5,618,702; 5,614,388; 5,610,017; 5,602,756; 5,599,674; 5,589,333; 5,585,238; 5,576,197; 5,565,340; 5,565,339; 5,556,774; 5,556,773; 5,538,871; 5,527,898; 5,527,510; 5,514,568; 5,512,463; 5,512,462; 5,501,947; 5,494,795; 5,491,225; 5,487,993; 5,487,985; 5,484,699; 5,476,774; 5,475,610; 5,447,839; 5,437,975; 5,436,144; 5,426,026; 5,420,009; 5,411,876; 5,393,657; 5,389,512; 5,364,790; 5,364,758; 5,340,728; 5,283,171; 5,279,952; 5,254,469; 5,241,363; 5,232,829; 5,231,015; 5,229,297; 5,224,778; 5,219,727; 5,213,961; 5,198,337; 5,187,060; 5,142,033; 5,091,310; 5,082,780; 5,066,584; 5,023,171 and 5,008,182 may also be employed in the practice of the present invention. PCR involves the use of a thermostable DNA polymerase, known sequences as primers, and heating cycles, which separate the replicating deoxyribonucleic acid (DNA), strands and exponentially amplify a gene of interest. Any type of PCR, such as quantitative PCR, RT-PCR, hot start PCR, LAPCR, multiplex PCR, touchdown PCR, etc., may be used. Advantageously, real-time PCR is used. In general, the PCR amplification process involves a cyclic enzymatic chain reaction for preparing exponential quantities of a specific nucleic acid sequence. It requires a small amount of a sequence to initiate the chain reaction and oligonucleotide primers that will hybridize to the sequence. In PCR the primers are annealed to denatured nucleic acid followed by extension with an inducing agent (enzyme) and nucleotides. This results in newly synthesized extension products. Since these newly synthesized sequences become templates for the primers, repeated cycles of denaturing, primer annealing, and extension results in exponential accumulation of the specific sequence being amplified. The extension product of the chain reaction will be a discrete nucleic acid duplex with a termini corresponding to the ends of the specific primers employed.

By the terms "enzymatically amplify" or "amplify" is meant, for the purposes of the specification or claims, DNA amplification, i.e., a process by which nucleic acid sequences are amplified in number. There are several means for enzymatically amplifying nucleic acid sequences. Currently the most commonly used method is the polymerase chain reaction (PCR). Other amplification methods include LCR (ligase chain reaction) which utilizes DNA ligase, and a probe consisting of two halves of a DNA segment that is complementary to the sequence of the DNA to be amplified, enzyme QB replicase and a ribonucleic acid (RNA) sequence template attached to a probe complementary to the DNA to be copied which is used to make a DNA template for exponential production of complementary RNA; strand displacement amplification (SDA); Qβ replicase amplification (QβRA); self-sustained replication (3SR); and NASBA (nucleic acid sequence-based amplification), which can be performed on RNA or DNA as the nucleic acid sequence to be amplified.

A "fragment" of a molecule such as a protein or nucleic acid is meant to refer to any portion of the amino acid or nucleotide genetic sequence.

As used herein, the term "genome" refers to all the genetic material in the chromosomes of a particular organism. Its size is generally given as its total number of base pairs. Within the genome, the term "gene" refers to an ordered sequence of nucleotides located in a particular position on a particular chromosome that encodes a specific functional product (e.g., a protein or RNA molecule). In general, an animal's genetic characteristics, as defined by the nucleotide sequence of its genome, are known as its "genotype," while the animal's physical traits are described as its "phenotype."

By "heterozygous" or "heterozygous polymorphism" is meant that the two alleles of a diploid cell or organism at a given locus are different, that is, that they have a different nucleotide exchanged for the same nucleotide at the same place in their sequences.

By "homozygous" or "homozygous polymorphism" is meant that the two alleles of a diploid cell or organism at a given locus are identical, that is, that they have the same nucleotide for nucleotide exchange at the same place in their sequences.

By "hybridization" or "hybridizing," as used herein, is meant the formation of A-T and C-G base pairs between the nucleotide sequence of a fragment of a segment of a polynucleotide and a complementary nucleotide sequence of an oligonucleotide. By complementary is meant that at the locus of each A, C, G or T (or U in a ribonucleotide) in the fragment sequence, the oligonucleotide sequenced has a T, G, C or A, respectively. The hybridized fragment/oligonucleotide is called a "duplex."

A "hybridization complex", such as in a sandwich assay, means a complex of nucleic acid molecules including at least the target nucleic acid and a sensor probe. It may also include an anchor probe.

As used herein, the term "locus" or "loci" refers to the site of a gene on a chromosome. Pairs of genes, known as "alleles" control the hereditary trait produced by a gene locus. Each animal's particular combination of alleles is referred to as its "genotype". Where both alleles are identical the individual is said to be homozygous for the trait controlled by that gene pair; where the alleles are different, the individual is said to be heterozygous for the trait.

A "melting temperature" is meant the temperature at which hybridized duplexes dehybridize and return to their single-stranded state. Likewise, hybridization will not occur in the first place between two oligonucleotides, or, herein, an oligonucleotide and a fragment, at temperatures above the melting temperature of the resulting duplex. It is presently advantageous that the difference in melting point temperatures of oligonucleotide-fragment duplexes of this invention be from about 1° C. to about 10° C. so as to be readily detectable.

As used herein, the term "nucleic acid molecule" is intended to include DNA molecules (e.g., cDNA or genomic DNA), RNA molecules (e.g., mRNA), analogs of the DNA or RNA generated using nucleotide analogs, and derivatives, fragments and homologs thereof. The nucleic acid molecule can be single-stranded or double-stranded, but advantageously is double-stranded DNA. "DNA" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). An "isolated" nucleic acid molecule is one that is separated from other nucleic acid molecules that are present in the natural source of the nucleic acid.

A "nucleoside" refers to a base linked to a sugar. The base may be adenine (A), guanine (G) (or its substitute, inosine (I)), cytosine (C), or thymine (T) (or its substitute, uracil (U)). The sugar may be ribose (the sugar of a natural nucleotide in RNA) or 2-deoxyribose (the sugar of a natural nucleotide in DNA). A "nucleotide" refers to a nucleoside linked to a single phosphate group.

As used herein, the term "oligonucleotide" refers to a series of linked nucleotide residues, which oligonucleotide has a sufficient number of nucleotide bases to be used in a PCR reaction. A short oligonucleotide sequence may be based on, or designed from, a genomic or cDNA sequence and is used to amplify, confirm, or reveal the presence of an identical, similar or complementary DNA or RNA in a particular cell or tissue. Oligonucleotides may be chemically synthesized and may be used as primers or probes. Oligonucleotide means any nucleotide of more than 3 bases in length used to facilitate detection or identification of a target nucleic acid, including probes and primers.

A "polymerase" is an enzyme that catalyzes the sequential addition of monomeric units to a polymeric chain, or links two or more monomeric units to initiate a polymeric chain. The "polymerase" will work by adding monomeric units whose identity is determined by and which is complementary to a template molecule of a specific sequence. For example, DNA polymerases such as DNA pol 1 and Taq polymerase add deoxyribonucleotides to the 3' end of a polynucleotide chain in a template-dependent manner, thereby synthesizing a nucleic acid that is complementary to the template molecule. Polymerases may be used either to extend a primer once or repetitively or to amplify a polynucleotide by repetitive priming of two complementary strands using two primers. A "thermostable polymerase" refers to a DNA or RNA polymerase enzyme that can withstand extremely high temperatures, such as those approaching 100° C. Often, thermostable polymerases are derived from organisms that live in extreme temperatures, such as Thermus aquaticus. Examples of thermostable polymerases include Taq, Tth, Pfu, Vent, deep vent, UlTma, and variations and derivatives thereof.

A "polynucleotide" refers to a linear chain of nucleotides connected by a phosphodiester linkage between the 3'-hydroxyl group of one nucleoside and the 5'-hydroxyl group of a second nucleoside which in turn is linked through its 3'-hydroxyl group to the 5'-hydroxyl group of a third nucleoside and so on to form a polymer comprised of nucleosides linked by a phosphodiester backbone. A "modified polynucleotide" refers to a polynucleotide in which one or more natural nucleotides have been partially,substantially, or completely replaced with modified nucleotides.

A "primer" is an oligonucleotide, the sequence of at least of portion of which is complementary to a segment of a template DNA which is to be amplified or replicated. Typically primers are used in performing the polymerase chain reaction (PCR). A primer hybridizes with (or "anneals" to) the template DNA and is used by the polymerase enzyme as the starting point for the replication/amplification process. The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hyhridize therewith and thereby form the template for the synthesis of the extension product.

"Probes" refer to oligonucleotides nucleic acid sequences of variable length, used in the detection of identical, similar, or complementary nucleic acid sequences by hybridization. An oligonucleotide sequence used as a detection probe may be labeled with a detectable moiety.

The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracil, other sugars and linking groups such as fluororibose and thiolate, and nucleotide branches. The sequence of nucleotides may be further modified after polymerization, such as by conjugation, with a labeling component. Other types of modifications included in this definition are caps, substitution of one or more of the naturally occurring nucleotides with an analog, and introduction of means for attaching the polynucleotide to proteins, metal ions, labeling components, other polynucleotides or solid support.

An "isolated" polynucleotide or polypeptide is one that is substantially pure of the materials with which it is associated in its native environment. By substantially free, is meant at least 50%, at least 55%, at least 60%, at least 65%, at advantageously at least 70%, at least 75%, more advantageously at least 80%, at least 85%, even more advantageously at least 90%, at least 91%, at least 92%, at least 93%, at least 94%, at least 95%, at least 96%, at least 97%, most advantageously at least 98%, at least 99%, at least 99.5%, at least 99.9% free of these materials.

An "isolated" nucleic acid molecule is a nucleic acid molecule separate and discrete from the whole organism with which the molecule is found in nature; or a nucleic acid molecule devoid, in whole or part, of sequences normally associated with it in nature; or a sequence, as it exists in nature, but having heterologous sequences (as defined below) in association therewith.

The term "polynucleotide encoding a protein" as used herein refers to a DNA fragment or isolated DNA molecule encoding a protein, or the complementary strand thereto; but, RNA is not excluded, as it is understood in the art that thymidine (T) in a DNA sequence is considered equal to uracil (U) in an RNA sequence. Thus, RNA sequences for use in the invention, e.g., for use in RNA vectors, can be derived from DNA sequences, by thymidine (T) in the DNA sequence being considered equal to uracil (U) in RNA sequences.

A DNA "coding sequence" or a "nucleotide sequence encoding" a particular protein, is a DNA sequence which is transcribed and translated into a polypeptide in vitro or in vivo when placed under the control of appropriate regulatory elements. The boundaries of the coding sequence are determined by a start codon at the 5' (amino) terminus and a translation stop codon at the 3' (carboxy) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A transcription termination sequence will usually be located 3' to the coding sequence. "Homology" refers to the percent identity between two polynucleotide or two polypeptide moieties. Two DNA, or two polypeptide sequences are "substantially homologous" to each other when the sequences exhibit at least about 80%, 81%, 82%, 83%, 84%, 85%, 86%, 87%, 88%, 89%, preferably at least about 90%, 91%, 92%, 93%, 94% and most preferably at least about 95%, 96%, 97%, 98%, 99%, 99.5%, 99.9% sequence identity over a defined length of the molecules. As used herein, substantially homologous also refers to sequences showing complete identity (100% sequence identity) to the specified DNA or polypeptide sequence.

Homology can be determined by hybridization of polynucleotides under conditions that form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al. supra; DNA Cloning, supra; Nucleic Acid Hybridization, supra.

Two nucleic acid fragments are considered to be "selectively hybridizable" to a polynucleotide if they are capable of specifically hybridizing to a nucleic acid or a variant thereof or specifically priming a polymerase chain reaction: (i) under typical hybridization and wash conditions, as described, for example, in Sambrook et al. supra and Nucleic Acid Hybridization, supra, (ii) using reduced stringency wash conditions that allow at most about 25-30% basepair mismatches, for example: 2×SSC, 0.1 % SDS, room temperature twice, 30 minutes each; then 2×SSC, 0.1% SDS, 37° C. once, 30 minutes; then 2 ×SSC room temperature twice, 10 minutes each, or (iii) selecting primers for use in typical polymerase chain reactions (PCR) under standard conditions (described for example, in Saiki, et al. (1988) Science 239:487-491).

The term "capable of hybridizing under stringent conditions" as used herein refers to annealing a first nucleic acid to a second nucleic acid under stringent conditions as defined below. Stringent hybridization conditions typically permit the hybridization of nucleic acid molecules having at least 70% nucleic acid sequence identity with the nucleic acid molecule being used as a probe in the hybridization reaction. For example, the first nucleic acid may be a test sample or probe, and the second nucleic acid may be the sense or antisense strand of a nucleic acid or a fragment thereof. Hybridization of the first and second nucleic acids may be conducted under stringent conditions, e.g., high temperature and/or low salt content that tend to disfavor hybridization of dissimilar nucleotide sequences. Alternatively, hybridization of the first and second nucleic acid may be conducted under reduced stringency conditions, e.g. low temperature and/or high salt content that tend to favor hybridization of dissimilar nucleotide sequences. Low stringency hybridization conditions may be followed by high stringency conditions or intermediate medium stringency conditions to increase the selectivity of the binding of the first and second nucleic acids. The hybridization conditions may further include reagents such as, but not limited to, dimethyl sulfoxide (DMSO) or formamide to disfavor still further the hybridization of dissimilar nucleotide sequences. A suitable hybridization protocol may, for example, involve hybridization in 6 ×SSC (wherein 1 ×SSC comprises 0.015 M sodium citrate and 0.15 M sodium chloride), at 65° Celsius in an aqueous solution, followed by washing with 1 ×SSC at 65° C. Formulae to calculate appropriate hybridization and wash conditions to achieve hybridization permitting 30% or less mismatch between two nucleic acid molecules are disclosed, for example, in Meinkoth et al. (1984) Anal. Biochem. 138: 267-284; the content of which is herein incorporated by reference in its entirety. Protocols for hybridization techniques are well known to those of skill in the art and standard molecular biology manuals may be consulted to select a suitable hybridization protocol without undue experimentation. See, for example, Sambrook et al. (2001) Molecular Cloning: A Laboratory Manual, 3rd ed., Cold Spring Harbor Press, the contents of which are herein incorporated by reference in their entirety.

Typically, stringent conditions will be those in which the salt concentration is less than about 1.5 M sodium ion, typically about 0.01 to 1.0 M Na ion concentration (or other salts) from about pH 7.0 to about pH 8.3 and the temperature is at least about 30° Celsius for short probes (e.g.,10 to 50 nucleotide) an at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° Celsius, and a wash in 1-2 ×SSC at 50 to 55° Celsius. Exemplary moderate stringency conditions include hybridization in 40 to 45% formamide, 1 M NaCl, 1% SDS at 37° Celsius, and a wash in 0.5-1 ×SSC at 55 to 60° Celsius. Exemplary high stringency conditions include hybridization in 50% formamide, 1 M NaCl, 1% SDS at 37° Celsius, and a wash in 0.1 ×SSC at 60 to 65° Celsius.

Methods and materials of the invention may be used more generally to evaluate a DNA sample from an animal, genetically type an individual animal, and detect genetic differences in animals. In particular, a sample of genomic DNA from an animal may be evaluated by reference to one or more controls to determine if a SNP, or group of SNPs, in a gene is present. Any method for determining genotype can be used for determining the genotype in the present invention. Such methods include, but are not limited to, amplimer sequencing, DNA sequencing, fluorescence spectroscopy, fluorescence resonance energy transfer (or "FRET")-based hybridization analysis, high throughput screening, mass spectroscopy, microsatellite analysis, nucleic acid hybridization, polymerase chain reaction (PCR), RFLP analysis and size chromatography (e.g., capillary or gel chromatography), all of which are well known to one of skill in the art. In particular, methods for determining nucleotide polymorphisms, particularly single nucleotide polymorphisms, are described in U.S. Patent Nos. 6,514,700; 6,503,710; 6,468,742; 6,448,407; 6,410,231; 6,383,756; 6,358,679; 6,322,980; 6,316,230; and 6,287,766 and reviewed by Chen and Sullivan, Pharmacogenomics J 2003;3(2):77-96, the disclosures of which are incorporated by reference in their entireties. Genotypic data useful in the methods of the invention and methods for the identification and selection of animal traits are based on the presence of SNPs.

A "restriction fragment" refers to a fragment of a polynucleotide generated by a restriction endonuclease (an enzyme that cleaves phosphodiester bonds within a polynucleotide chain) that cleaves DNA in response to a recognition site on the DNA. The recognition site (restriction site) consists of a specific sequence of nucleotides typically about 4-8 nucleotides long.

A "single nucleotide polymorphism" or "SNP" refers to a variation in the nucleotide sequence of a polynucleotide that differs from another polynucleotide by a single nucleotide difference. For example, without limitation, exchanging one A for one C, G or T in the entire sequence of polynucleotide constitutes a SNP. It is possible to have more than one SNP in a particular polynucleotide. For example, at one position in a polynucleotide, a C may be exchanged for a T, at another position a G may be exchanged for an A and so on. When referring to SNPs, the polynucleotide is most often DNA.

As used herein, a "template" refers to a target polynucleotide strand, for example, without limitation, an unmodified naturally-occurring DNA strand, which a polymerase uses as a means of recognizing which nucleotide it should next incorporate into a growing strand to polymerize the complement of the naturally-occurring strand. Such a DNA strand may be single-stranded or it may be part of a double-stranded DNA template. In applications of the present invention requiring repeated cycles of polymerization, e.g., the polymerase chain reaction (PCR), the template strand itself may become modified by incorporation of modified nucleotides, yet still serve as a template for a polymerase to synthesize additional polynucleotides.

A "thermocyclic reaction" is a multi-step reaction wherein at least two steps are accomplished by changing the temperature of the reaction.

A "variance" is a difference in the nucleotide sequence among related polynucleotides. The difference may be the deletion of one or more nucleotides from the sequence of one polynucleotide compared to the sequence of a related polynucleotide, the addition of one or more nucleotides or the substitution of one nucleotide for another. The terms "mutation," "polymorphism" and "variance" are used interchangeably herein. As used herein, the term "variance" in the singular is to be construed to include multiple variances; i.e., two or more nucleotide additions, deletions and/or substitutions in the same polynucleotide. A "point mutation" refers to a single substitution of one nucleotide for another.

As used herein, the terms "traits", "quality traits" or "physical characteristics" or "phenotypes" refer to advantageous properties of the animal resulting from genetics. Quality traits include, but are not limited to, the animal's genetic ability to efficiently metabolize energy, produce meat or milk, put on intramuscular fat. Physical characteristics include, but are not limited to, marbled, tender or lean meats. The terms may be used interchangeably.

A "computer system" refers to the hardware means, software means and data storage means used to compile the data of the present invention. The minimum hard ware means of computer-based systems of the invention may comprise a central processing unit (CPU), input means, output means, and data storage means. Desirably, a monitor is provided to visualize structure data. The data storage means may be RAM or other means for accessing computer readable media of the invention. Examples of such systems are microcomputer workstations available from Silicon Graphics Incorporated and Sun Microsystems running Unix based, Linux, Windows NT, XP or IBM OS/2 operating systems.

"Computer readable media" refers to any media which can be read and accessed directly by a computer, and includes, but is not limited to: magnetic storage media such as floppy discs, hard storage medium and magnetic tape; optical storage media such as optical discs or CD-ROM; electrical storage media such as RAM and ROM; and hybrids of these categories, such as magnetic/optical media. By providing such computer readable media, the data compiled on a particular animal can be routinely accessed by a user, e.g., a feedlot operator.

The term "data analysis module" is defined herein to include any person or machine, individually or working together, which analyzes the sample and determines the genetic information contained therein. The term may include a person or machine within a laboratory setting.

As used herein, the term "data collection module" refers to any person, object or system obtaining a tissue sample from an animal or embryo. By example and without limitation, the term may define, individually or collectively, the person or machine in physical contact with the animal as the sample is taken, the containers holding the tissue samples, the packaging used for transporting the samples, and the like. Advantageously, the data collector is a person. More advantageously, the data collector is a livestock farmer, a breeder or a veterinarian The term "network interface" is defined herein to include any person or computer system capable of accessing data, depositing data, combining data, analyzing data, searching data, transmitting data or storing data. The term is broadly defined to be a person analyzing the data, the electronic hardware and software systems used in the analysis, the databases storing the data analysis, and any storage media capable of storing the data. Non-limiting examples of network interfaces include people, automated laboratory equipment, computers and computer networks, data storage devices such as, but not limited to, disks, hard drives or memory chips.

The term "breeding history" as used herein refers to a record of the life of an animal or group of animals including, but not limited to, the location, breed, period of housing, as well as a genetic history of the animals, including parentage and descent therefrom, genotype, phenotype, transgenic history if relevant and the like.

The term "husbandry conditions" as used herein refers to parameters relating to the maintenance of animals including, but not limited to, shed or housing temperature, weekly mortality of a herd, water consumption, feed consumption, ventilation rate and quality, litter condition and the like.

The term "veterinary history" as used herein refers to vaccination data of an animal or group of animals, including, but not limited to, vaccine type(s), vaccine batch serial number(s), administered dose, target antigen, method of administering of the vaccine to the recipient animal(s), number of vaccinated animals, age of the animals and the vaccinator. Data relating to a serological or immunological response induced by the vaccine may also be included. "Veterinary history" as used herein is also intended to include the medication histories of the target animal(s) including, but not limited to drug and/or antibiotics administered to the animals including type of administered medication, quantity and dose rates, by whom and when administered, by what route, e.g., oral, subcutaneously and the like, and the response to the medication including desired and undesirable effects thereof.

The term "diagnostic data" as used herein refers to data relating to the health of the animal(s) other than data detailing the vaccination or medication history of the animal(s). For example, the diagnostic data may be a record of the infections experienced by the animal(s) and the response thereof to medications provided to treat such medications. Serological data including antibody or protein composition of the serum or other biofluids may also be diagnostic data useful to input in the methods of the invention. Surgical data pertaining to the animal(s) may be included, such as the type of surgical manipulation, outcome of the surgery and complications arising from the surgical procedure. "Diagnostic data" may also include measurements of such parameters as weight, morbidity, and other characteristics noted by a veterinary service such as the condition of the skin, feet, etc.

The term "welfare data" as used herein refers to the collective accumulation of data pertaining to an animal or group of animals including, but not limited to, a breeding history, a veterinary history, a welfare profile, diagnostic data, quality control data, or any combination thereof.

The term "welfare profile" as used herein refers to parameters such as weight, meat density, crowding levels in breeding or rearing enclosures, psychological behavior of the animal, growth rate and quality and the like.

The term "quality control" as used herein refers to the desired characteristics of the animal(s). For non-poultry animals such as cattle and sheep for example, such parameters include muscle quantity and density, fat content, meat tenderness, milk yield and quality, breeding ability, and the like.

The term "performance parameters" as used herein refers to such factors as meat yield, breeding yield, dairy form, meat quality and yield, productive life and the like that may be the desired goals from the breeding and rearing of the animal(s). Performance parameters may be either generated from the animals themselves, or those parameters desired by a customer or the market.

The term "nutritional data" as used herein refers to the composition, quantity and frequency of delivery of feed, including water, provided to the animal(s).

The term "food safety" as used herein refers to the quality of the meat from a livestock animal, including, but not limited to, preparation time, place and manner, storage of the food product, transportation route, inspection records, texture, color, taste, odor, bacterial content, parasitic content and the like.

It will be apparent to those of skill in the art that the data relating to the health and maintenance of the animals may be variously grouped depending upon the source or intention of the data collector and any one grouping herein is not therefore intended to be limiting.

Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein.

In an embodiment wherein the gene of interest is bovine FABP, the bovine FABP nucleotide sequence can be selected from, but is not limited to, the sequence corresponding to FIG. 4, SEQ ID NO: 1 or a fragment thereof or a region of the bovine genome that comprises this sequence.

The present invention, therefore, provides isolated nucleic acids that may specifically hybridize to the nucleotide sequence corresponding to FIG. 4, SEQ ID NO: 1 or the complement thereof, and which comprises the polymorphic site corresponding to nucleotide position a G to C substitution at the 7516 nucleotide position of the FABP4 gene and a G to C substitution at position 7713 of the FABP4 gene.

The SNP advantageous in the present invention is associated with certain economically valuable and heritable traits relating to meat quality in bovines. Therefore, it is an object of the present invention to determine the genotype of a given animal of interest as defined by the FABP locus SNP according to the present invention. It is also contemplated that the genotype of the animal(s) may be defined by additional SNPs within the FABP gene or within other genes identified with desirable traits or other characteristics, and in particular by a panel or panels of SNPs.

There are many methods known in the art for determining the sequence of DNA in a sample, and for identifying whether a given DNA sample contains a particular SNP. Any such technique known in the art may be used in performance of the methods of the present invention.

The methods of the present invention allow animals with certain economically valuable heritable traits to be identified based on the presence of SNPs in their genomes and particularly with a SNP located within the FABP gene. The methods further allow, by computer-assisted methods of the invention, to correlate the SNP-associated traits with other data pertinent to the well-being and productive capacity of the animals, or group of animals.

To determine the genotype of a given animal according to the methods of the present invention, it is necessary to obtain a sample of genomic DNA from that animal. Typically, that sample of genomic DNA will be obtained from a sample of tissue or cells taken from that animal. A tissue or cell sample may be taken from an animal at any time in the lifetime of an animal but before the carcass identity is lost. The tissue sample can comprise hair, including roots, hide, bone, buccal swabs, blood, saliva, milk, semen, embryos, muscle or any internal organs. In the methods of the present invention, the source of the tissue sample, and thus also the source of the test nucleic acid sample, is not critical. For example, the test nucleic acid can be obtained from cells within a body fluid of the animal, or from cells constituting a body tissue of the animal. The particular body fluid from which cells are obtained is also not critical to the present invention. For example, the body fluid may be selected from the group consisting of blood, ascites, pleural fluid and spinal fluid. Furthermore, the particular body tissue from which cells are obtained is also not critical to the present invention. For example, the body tissue may be selected from the group consisting of skin, endometrial, uterine and cervical tissue. Both normal and tumor tissues can be used.

Typically, the tissue sample is marked with an identifying number or other indicia that relates the sample to the individual animal from which the sample was taken. The identity of the sample advantageously remains constant throughout the methods and systems of the invention thereby guaranteeing the integrity and continuity of the sample during extraction and analysis. Alternatively, the indicia may be changed in a regular fashion that ensures that the data, and any other associated data, can be related back to the animal from which the data was obtained.

The amount/size of sample required is known to those skilled in the art and for example, can be determined by the subsequent steps used in the method and system of the invention and the specific methods of analysis used. Ideally, the size/volume of the tissue sample retrieved should be as consistent as possible within the type of sample and the species of animal. For example, for cattle, non-limiting examples of sample sizes/methods include non-fatty meat: 0.0002 gm-10.0 gm; hide: 0.0004 gm-10.0 gm; hair roots: at least one and advantageously greater than five; buccal swabs: 15 to 20 seconds of rubbing with modest pressure in the area between outer lip and gum using, for example, a cytology brush; bone: 0.0002 gm-10.0 gm; blood: 30 µl to 50 ml.

Generally, the tissue sample is placed in a container that is labeled using a numbering system bearing a code corresponding to the animal, for example, to the animal's ear tag. Accordingly, the genotype of a particular animal is easily traceable at all times. The sampling device and/or container may be supplied to the farmer, a slaughterhouse or retailer. The sampling device advantageously takes a consistent and reproducible sample from individual animals while simultaneously avoiding any cross-contamination of tissue. Accordingly, the size and volume of sample tissues derived from individual animals would be consistent.

DNA can be isolated from the tissue/cells by techniques known to those skilled in the art (see, e.g., U.S. Pat. Nos. 6,548,256 and 5,989,431; Hirota et al. (1989) Jinrui Idengaku Zasshi. 34: 217-23 and John et al. (1991) Nucleic Acids Res. 19:408, the disclosures of which are incorporated by reference in their entireties). For example, high molecular weight DNA may be purified from cells or tissue using proteinase K extraction and ethanol precipitation. DNA, however, may be extracted from an animal specimen using any other suitable methods known in the art.

In one embodiment, the presence or absence of the SNP of any of the genes of the present invention may be determined by sequencing the region of the genomic DNA sample that spans the polymorphic locus. Many methods of sequencing genomic DNA are known in the art, and any such method can be used, see for example Sambrook et al. (2001) Molecular Cloning: A Laboratory Manual, 3rd ed., Cold Spring Harbor Press. For example, as described below, a DNA fragment spanning the location of the SNP of interest can be amplified using the polymerase chain reaction. The amplified region of DNA form can then be sequenced using any method known in the art, for example using an automatic nucleic acid sequencer. The detection of a given SNP can then be performed using hybridization of probes and or using PCR-based amplification methods. Such methods are described in more detail below.

The methods of the present invention may use oligonucleotides useful as primers to amplify specific nucleic acid sequences of the FABP4 gene, advantageously of the region encompassing a FABP4 SNP. Such fragments should be of sufficient length to enable specific annealing or hybridization to the nucleic acid sample. The sequences typically will be about 8 to about 44 nucleotides in length. Longer sequences, e.g., from about 14 to about 50, may be advantageous for certain embodiments. The design of primers is well known to one of ordinary skill in the art.

Inventive nucleic acid molecules include nucleic acid molecules having at least 70% identity or homology or similarity with a FABP4 gene or probes or primers derived therefrom such as at least 75% identity or homology or similarity, preferably at least 80% identity or homology or similarity, more preferably at least 85% identity or homology or similarity such as at least 90% identity or homology or similarity, more preferably at least 95% identity or homology or similarity such as at least 97% identity or homology or similarity. The nucleotide sequence similarity or homology or identity can be determined using the "Align" program of Myers and Miller, ("Optimal Alignments in Linear Space", CABIOS 4, 11-17, 1988) and available at NCBI. Alternatively or additionally, the terms "similarity" or "identity" or "homology", for instance, with respect to a nucleotide sequence, is intended to indicate a quantitative measure of homology between two sequences. The percent sequence similarity can be calculated as $(N_{ref}-N_{dif})*100/N_{ref}$, wherein $N_{dif}$ is the total number of non-identical residues in the two sequences when aligned and wherein $N_{ref}$ is the number of residues in one of the sequences. Hence, the DNA sequence AGTCAGTC will have a sequence similarity of 75% with the sequence AATCAATC ($N_{ref}=8$; $N_{dif}=2$). Alternatively or additionally, "similarity" with respect to sequences refers to the number of positions with identical nucleotides divided by the number of nucleotides in the shorter of the two sequences wherein alignment of the two sequences can be determined in accordance with the Wilbur and Lipman algorithm (Wilbur and Lipman, 1983 PNAS USA 80:726), for instance, using a window size of 20 nucleotides, a word length of 4 nucleotides, and a gap penalty of 4, and computer-assisted analysis and interpretation of the sequence data including alignment can be conveniently performed using commercially available programs (e.g., Intelligenetics™ Suite, Intelligenetics Inc. CA).. When RNA sequences are said to be similar, or have a degree of sequence identity with DNA sequences, thymidine (T) in the DNA sequence is considered equal to uracil (U) in the RNA sequence.

A probe or primer can be any stretch of at least 8, preferably at least 10, more preferably at least 12, 13, 14, or 15, such as at least 20, e.g., at least 23 or 25, for instance at least 27 or 30 nucleotides in a FABP gene which are unique to a FABP gene. As to PCR or hybridization primers or probes and optimal lengths therefor, reference is also made to Kajimura et al., GATA 7(4):71-79 (1990).

RNA sequences within the scope of the invention are derived from the DNA sequences, by thymidine (T) in the DNA sequence being considered equal to uracil (U) in RNA sequences.

The oligonucleotides can be produced by a conventional production process for general oligonucleotides. They can be produced, for example, by a chemical synthesis process or by a microbial process that makes use of a plasmid vector, a phage vector or the like. Further, it is suitable to use a nucleic acid synthesizer.

To label an oligonucleotide with the fluorescent dye, one of conventionally known labeling methods can be used (Tyagi & Kramer (1996) Nature Biotechnology 14: 303-308; Schofield et al. (1997) Appl. and Environ. Microbiol. 63: 1143-1147; Proudnikov & Mirzabekov (1996) Nucl. Acids Res. 24: 4532-4535). Alternatively, the oligonucleotide may be labeled with a radiolabel e.g., $^3H$, $^{125}I$, $^{35}S$, $^{14}C$, $^{32}P$, etc. Well-known labeling methods are described, for example, in Sambrook et al. (2001) Molecular Cloning: A Laboratory Manual, 3rd ed., Cold Spring Harbor Press. The label is coupled directly or indirectly to a component of the oligonucleotide according to methods well known in the art. Reversed phase chromatography or the like used to provide a nucleic acid probe for use in the present invention can purify the synthesized oligonucleotide labeled with a marker. An advantageous probe form is one labeled with a fluorescent dye at the 3'- or 5'-end and containing G or C as the base at the labeled end. If the 5'-end is labeled and the 3'-end is not labeled, the OH group on the C atom at the 3'-position of the 3'-end ribose or deoxyribose may be modified with a phosphate group or the like although no limitation is imposed in this respect.

During the hybridization of the nucleic acid target with the probes, stringent conditions may be utilized, advantageously along with other stringency affecting conditions, to aid in the hybridization. Detection by differential disruption is particularly advantageous to reduce or eliminate slippage hybridization among probes and target, and to promote more effective hybridization. In yet another aspect, stringency conditions may be varied during the hybridization complex stability determination so as to more accurately or quickly determine whether a SNP is present in the target sequence.

One method for determining the genotype at the polymorphic gene locus encompasses obtaining a nucleic acid sample, hybridizing the nucleic acid sample with a probe, and disrupting the hybridization to determine the level of disruption energy required wherein the probe has a different disruption energy for one allele as compared to another allele. In one example, there can be a lower disruption energy, e.g., melting temperature, for an allele that harbors a cytosine residue at a polymorphic locus, and a higher required energy for an allele with a different residue at that polymorphic locus. This can be achieved where the probe has 100% homology with one allele (a perfectly matched probe), but has a single mismatch with the alternative allele. Since the perfectly matched probe is bound more tightly to the target DNA than the mismatched probe, it requires more energy to cause the hybridized probe to dissociate.

In a further step of the above method, a second ("anchor") probe may be used. Generally, the anchor probe is not specific to either allele, but hybridizes regardless of what nucleotide is present at the polymorphic locus. The anchor probe does not affect the disruption energy required to disassociate the hybridization complex but, instead, contains a complementary label for using with the first ("sensor") probe.

Hybridization stability may be influenced by numerous factors, including thermoregulation, chemical regulation, as well as electronic stringency control, either alone or in combination with the other listed factors. Through the use of stringency conditions, in either or both of the target hybridization step or the sensor oligonucleotide stringency step, rapid completion of the process may be achieved. This is desirable to achieve properly indexed hybridization of the target DNA to attain the maximum number of molecules at a test site with an accurate hybridization complex. By way of example, with the use of stringency, the initial hybridization step may be completed in ten minutes or less, more advantageously five minutes or less, and most advantageously two minutes or less. Overall, the analytical process may be completed in less than half an hour.

In one mode, the hybridization complex is labeled and the step of determining the amount of hybridization includes detecting the amounts of labeled hybridization complex at the test sites. The detection device and method may include, but is not limited to, optical imaging, electronic imaging, imaging with a CCD camera, integrated optical imaging, and mass spectrometry. Further, the amount of labeled or unlabeled probe bound to the target may be quantified. Such quantification may include statistical analysis. The labeled portion of the complex may be the target, the stabilizer, the probe or the hybridization complex in toto. Labeling may be by fluorescent labeling selected from the group of, but not limited to, Cy3, Cy5, Bodipy Texas Red, Bodipy Far Red, Lucifer Yellow, Bodipy 630/650-X, Bodipy R6G-X and 5-CR6G. Colormetric labeling, bioluminescent labeling and/or chemiluminescent labeling may further accomplish labeling. Labeling further may include energy transfer between molecules in the hybridization complex by perturbation analysis, quenching, electron transport between donor and acceptor molecules, the latter of which may be facilitated by double stranded match hybridization complexes. Optionally, if the hybridization complex is unlabeled, detection may be accomplished by measurement of conductance differential between double stranded and non-double stranded DNA. Further, direct detection may be achieved by porous silicon-based optical interferometry or by mass spectrometry. In using mass spectrometry no fluorescent or other label is necessary. Rather detection is obtained by extremely high levels of mass resolution achieved by direct measurement, for example, by time of flight (TOF) or by electron spray ionization (ESI). Where mass spectrometry is contemplated, probes having a nucleic acid sequence of 50 bases or less are advantageous.

The label may be amplified, and may include, for example, branched or dendritic DNA. If the target DNA is purified, it may be un-amplified or amplified. Further, if the purified target is amplified and the amplification is an exponential method, it may be, for example, PCR amplified DNA or strand displacement amplification (SDA) amplified DNA. Linear methods of DNA amplification such as rolling circle or transcriptional runoff may also be used.

Where it is desired to amplify a fragment of DNA that comprises a SNP according to the present invention, the forward and reverse primers may have contiguous stretches of about 8, 9, 10, 11, 12, 13, 14, 15, 16, 17, 18, 19, 20, 21, 22, 23, 24, 25, 26, 27, 28, 29, 30 or any other length up to and including about 50 nucleotides in length. The sequences to which the forward and reverse primers anneal are advantageously located on either side of the particular nucleotide position that is substituted in the SNP to be amplified.

A detectable label can be incorporated into a nucleic acid during at least one cycle of an amplification reaction. Spectroscopic, photochemical, biochemical, immunochemical, electrical, optical or chemical means can detect such labels. Useful labels in the present invention include fluorescent dyes (e.g., fluorescein isothiocyanate, Texas red, rhodamine, and the like), radiolabels (e.g., $^{3}$H, $^{125}$I, $^{35}$S, $^{14}$C, $^{32}$P, etc.), enzymes (e.g. horseradish peroxidase, alkaline phosphatase etc.) calorimetric labels such as colloidal gold or colored glass or plastic (e.g. polystyrene, polypropylene, latex, etc.) beads. The label is coupled directly or indirectly to a component of the assay according to methods well known in the art. As indicated above, a wide variety of labels are used, with the choice of label depending on sensitivity required, ease of conjugation with the compound, stability requirements, available instrumentation, and disposal provisions. Non-radioactive labels are often attached by indirect means. Polymerases can also incorporate fluorescent nucleotides during synthesis of nucleic acids.

Reagents allowing the sequencing of reaction products can be utilized herein. For example, chain-terminating nucleotides will often be incorporated into a reaction product during one or more cycles of a reaction. Commercial kits containing the reagents most typically used for these methods of DNA sequencing are available and widely used. PCR exonuclease digestion methods for DNA sequencing can also be used. Many methods of sequencing genomic DNA are known in the art, and any such method can be used, see for example Sambrook et al. (2001) Molecular Cloning: A Laboratory Manual, 3rd ed., Cold Spring Harbor Press. For example, as described below, a DNA fragment spanning the location of the SNP of interest can amplified using the polymerase chain reaction or some other cyclic polymerase mediated amplification reaction. The amplified region of DNA can then be sequenced using any method known in the art. Advantageously, the nucleic acid sequencing is by automated methods (reviewed by Meldrum, (2000) Genome Res. 10:1288-303, the disclosure of which is incorporated by reference in its entirety), for example using a Beckman CEQ 8000 Genetic Analysis System (Beckman Coulter Instruments, Inc.). Methods for sequencing nucleic acids include, but are not limited to, automated fluorescent DNA sequencing (see, e.g., Watts & MacBeath, (2001) Methods Mol Biol. 167:153-70 and MacBeath et al. (2001) Methods Mol Biol. 167:119-52), capillary electrophoresis (see, e.g., Bosserhoff et al. (2000) Comb Chem High Throughput Screen. 3:455-66), DNA sequencing chips (see, e.g., Jain, (2000) Pharmacogenomics. 1:89-307), mass spectrometry (see, e.g., Yates, (2000) Trends Genet. 16: 5-8), pyrosequencing (see, e.g., Ronaghi, (2001) Genome Res. 11: 3-11), and ultrathin-layer gel electrophoresis (see, e.g., Guttman & Ronai, (2000) Electrophoresis. 21: 3952-64), the disclosures of which are hereby incorporated by reference in their entireties. The sequencing can also be done by a commercial company. Examples of such companies include, but are not limited to, the University of Georgia Molecular Genetics Instrumentation Facility (Athens, Ga.) or SeqWright DNA Technologies Services (Houston, Tex.).

A SNP-specific probe can also be used in the detection of the SNP in amplified specific nucleic acid sequences of the target gene, such as the amplified PCR products generated using the primers described above. In certain embodiments, these SNP-specific probes consist of oligonucleotide fragments. Advantageously, the fragments are of sufficient length to provide specific hybridization to the nucleic acid sample. The use of a hybridization probe of between 10 and 50 nucleotides in length allows the formation of a duplex molecule that is both stable and selective. Molecules having complementary sequences over stretches greater than 12 bases in length are generally advantageous, in order to increase stability and selectivity of the hybrid, and thereby improve the quality and degree of particular hybrid molecules obtained. One will generally prefer to design nucleic acid molecules having stretches of 16 to 24 nucleotides, or even longer where desired. A tag nucleotide region may be included, as at the 5' end of the primer that may provide a site to which an oligonucleotide sequencing primer may hybridize to facilitate the sequencing of multiple PCR samples.

The probe sequence must span the particular nucleotide position that may be substituted in the particular SNP to be detected. Advantageously, two or more different "allele-specific probes" may be used for analysis of a SNP, a first allele-specific probe for detection of one allele, and a second allele-specific probe for the detection of the alternative allele.

It will be understood that this invention is not limited to the particular primers and probes disclosed herein and is intended to encompass at least nucleic acid sequences that are hybridizable to the nucleotide sequence disclosed herein, the complement or a fragment thereof, or are functional sequence analogs of these sequences. It is also contemplated that a particular trait of an animal may be determined by using a panel of SNPs associated with that trait. Several economically relevant traits may be characterized by the presence or absence of one or more SNPs and by a plurality of SNPs in different genes. One or more panels of SNPs may be used in the methods of the invention to define the phenotypic profile of the subject animal.

Homologs (i.e., nucleic acids derived from other species) or other related sequences (e.g., paralogs) can be obtained under conditions of standard or stringent hybridization conditions with all or a portion of the particular sequence as a probe using methods well known in the art for nucleic acid hybridization and cloning.

The genetic markers, probes thereof, methods, and kits of the invention are also useful in a breeding program to select for breeding those animals having desirable phenotypes for various economically important traits, such as improved meat quality and yield, in particular meat tenderness. Continuous selection and breeding of animals, such as livestock, that are at least heterozygous and advantageously homozygous for desirable alleles of the FABP gene polymorphic sites associated with economically relevant traits of growth, feed intake, efficiency and carcass merit, would lead to a breed, line, or population having higher numbers of offspring with economically relevant traits of growth, feed intake, efficiency and carcass merit. Thus, the FABP SNPs of the present invention can be used as a selection tool.

Desirable phenotypes include, but are not limited to, feed intake, growth rate, body weight, carcass merit and composition, and milk yield. Specific carcass traits with desirable phenotypes include, but are not limited to, additional carcass value (additional carc value, $), average daily gain (ADG, lb/d), backfat thickness (BFAT, in), calculated live weight (Calc Lv Wt, lb), calculated yield grade (cYG), days on feed (DOF, d), dressing percentage (DP, %), dry matter intake (DMI, lb), dry matter intake per day on feed (DMI per DOF, lb/d), hot carcass weight (HCW, lb), hot carcass weight value (HCW value, $), intramuscular fat content (IMF%, %), marbling score (MBS, 10 to 99), marbling score divided by days on feed (MBS/DOF), quality grade, less than or equal to select versus greater than or equal to choice (QG, <Se vs, >Ch), ribeye area (REA, $in^2$), ribeye area per hundred weight HCW (REA/cwt HCW, $in^2$/100 lb hot carcass weight (HCW) and subcutaneous fat depth (SFD).

One aspect of the present invention provides for grouping animals and methods for managing livestock production comprising grouping livestock animals such as cattle according the genotype as defined by panels of SNPs, each panel comprising at least one SNP, one or more of which are in the FABP gene of the present invention. Other SNPs that may be included in panels of SNPs include, but not limited to, SNPs found in the calpastatin gene, GHR gene, ghrelin gene, leptin gene, NPY gene, ob gene, TFAM gene, UASMS1 gene, UASMS2 gene, UASMS3 gene and/or the UCP2 gene. The genetic selection and grouping methods of the present invention can be used in conjunction with other conventional phenotypic grouping methods such as grouping animals by visible characteristics such as weight, frame size, breed traits, and the like. The methods of the present invention provide for producing cattle having improved heritable traits, and can be used to optimize the performance of livestock herds in areas such as breeding, feed intake, carcass/meat quality and milk production. The present invention provides methods of screening livestock to determine those more likely to develop a desired body condition by identifying the presence or absence of one or more gene polymorphisms correlated with meat quality.

As described above, and in the Examples, there are various phenotypic traits with which the SNPs of the present invention may be associated. Each of the phenotypic and genetic traits can be tested using the methods described in the Examples, or using any suitable methods known in the art. Using the methods of the invention, a farmer, or feedlot operator, or the like, can group cattle according to each animal's genetic propensity for a desired trait such as growth rate, feed intake or feeding behavior, as determined by SNP genotype. The cattle are tested to determine homozygosity or heterozygosity with respect to the SNP alleles of one or more genes so that they can be grouped such that each pen contains cattle with like genotypes. Each pen of animals is then fed and otherwise maintained in a manner and for a time determined by the feedlot operator, and then slaughtered.

The individual genotypic data derived from a panel or panels of SNPs for each animal or a herd of animals can be recorded and associated with various other data of the animal, e.g. health information, parentage, husbandry conditions, vaccination history, herd records, subsequent food safety data and the like. Such information can be forwarded to a government agency to provide traceability of an animal or meat product, or it may serve as the basis for breeding, feeding and marketing information. Once the data has or has not been associated with other data, the data is stored in an accessible database, such as, but not limited to, a computer database or a microchip implanted in the animal. The methods of the invention may provide an analysis of the input data that may be compared with parameters desired by the operator. These parameters include, but are not limited to, such as breeding goals, egg laying targets, vaccination levels of a herd. If the performance or properties of the animals deviates from the desired goals, the computer-based methods may trigger an alert to allow the operator to adjust vaccination doses, medications, feed etc accordingly.

The results of the analysis provide data that are associated with the individual animal or to the herd, in whole or in part, from which the sample was taken. The data are then kept in an accessible database, and may or may not be associated with other data from that particular individual or from other animals.

Data obtained from individual animals may be stored in a database that can be integrated or associated with and/or cross-matched to other databases. The database along with the associated data allows information about the individual animal to be known through every stage of the animal's life, i.e., from conception to consumption of the animal product.

The accumulated data and the combination of the genetic data with other types of data of the animal provides access to information about parentage, identification of herd, health information including vaccinations, exposure to diseases, feedlot location, diet and ownership changes. Information such as dates and results of diagnostic or routine tests are easily stored and attainable. Such information would be especially valuable to companies, particularly those who seek superior breeding lines.

Each animal may be provided with a unique identifier. The animal can be tagged, as in traditional tracing programs or have implant computer chips providing stored and readable data or provided with any other identification method which associates the animal with its unique identifier.

The database containing the SNP-based genotype results for each animal or the data for each animal can be associated or linked to other databases containing data, for example, which may be helpful in selecting traits for grouping or sub-grouping of an animal. For example, and not for limitation, data pertaining to animals having particular vaccination or medication protocols, can optionally be further linked with data pertaining to animals having food from certain food sources. The ability to refine a group of animals is limited only by the traits sought and the databases containing information related to those traits.

Databases that can usefully be associated with the methods of the invention include, but are not limited to, specific or general scientific data. Specific data includes, but is not limited to, breeding lines, sires, dames, and the like, other animals' genotypes, including whether or not other specific animals possess specific genes, including transgenic genetic elements, location of animals which share similar or identical genetic characteristics, and the like. General data includes, but is not limited to, scientific data such as which genes encode for specific quality characteristics, breed association data, feed data, breeding trends, and the like.

One method of the present invention includes providing the animal owner or customer with sample collection equipment, such as swabs and tags useful for collecting samples from which genetic data may be obtained. Advantageously, the packaging is encoded with a bar code label. The tags are encoded with the same identifying indicia, advantageously with a matching bar code label. Optionally, the packaging contains means for sending the tags to a laboratory for analysis. The optional packaging is also encoded with identifying indicia, advantageously with a bar code label.

The method optionally includes a system wherein a database account is established upon ordering the sampling equipment. The database account identifier corresponds to the identifying indicia of the tags and the packaging. Upon shipment of the sampling equipment in fulfillment of the order, the identifying indicia are recorded in a database. Advantageously, the identifier is a bar code label which is scanned when the tags are sent. When the tags are returned to the testing facility, the identifier is again recorded and matched to the information previously recorded in the database upon shipment of the vial to the customer. Once the genotyping is completed, the information is recorded in the database and coded with the unique identifier. Test results are also provided to the customer or animal owner.

The data stored in the genotype database can be integrated with or compared to other data or databases for the purpose of identifying animals based on genetic propensities. Other data or databases include, but are not limited to, those containing information related to SNP-based DNA testing, vaccination, Sure Health pre-conditioning program, estrus and pregnancy results, hormone levels, food safety/contamination, somatic cell counts, mastitis occurrence, diagnostic test results, milk protein levels, milk fat, vaccine status, health records, mineral levels, trace mineral levels, herd performance, and the like.

The present invention, therefore, encompasses computer-assisted methods for tracking the breeding and veterinary histories of livestock animals encompassing using a computer-based system comprising a programmed computer comprising a processor, a data storage system, an input device and an output device, and comprising the steps of generating a profile of a livestock animal by inputting into the programmed computer through the input device genotype data of the animal, wherein the genotype may be defined by a panel of at least two single nucleotide polymorphisms that predict at least one physical trait of the animal, inputting into the programmed computer through the input device welfare data of the animal, correlating the inputted welfare data with the phenotypic profile of the animal using the processor and the data storage system, and outputting a profile of the animal or group of animals to the output device.

The databases and the analysis thereof will be accessible to those to whom access has been provided. Access can be provided through rights to access or by subscription to specific portions of the data. For example, the database can be accessed by owners of the animal, the test site, the entity providing the sample to the test site, feedlot personnel, and veterinarians. The data can be provided in any form such as by accessing a website, fax, email, mailed correspondence, automated telephone, or other methods for communication. These data can also be encoded on a portable storage device, such as a microchip, that can be implanted in the animal. Advantageously, information can be read and new information added without removing the microchip from the animal.

The present invention comprises systems for performing the methods disclosed herein. Such systems comprise devices, such as computers, internet connections, servers, and storage devices for data. The present invention also provides for a method of transmitting data comprising transmission of information from such methods herein discussed or steps thereof, e.g., via telecommunication, telephone, video conference, mass communication, e.g., presentation such as a computer presentation (e.g., POWERPOINT), internet, email, documentary communication such as computer programs (e.g., WORD) and the like.

Systems of the present invention may comprise a data collection module, which includes a data collector to collect data from an animal or embryo and transmit the data to a data analysis module, a network interface for receiving data from the data analysis module, and optionally further adapted to combine multiple data from one or more individual animals, and to transmit the data via a network to other sites, or to a storage device.

More particularly, systems of the present invention comprise a data collection module, a data analysis module, a network interface for receiving data from the data analysis module, and optionally further adapted to combine multiple data from one or more individual animals, and to transmit the data via a network to other sites, and/or a storage device. For example, the data collected by the data collection module leads to a determination of the absence or presence of a SNP of a gene in the animal or embryo, and for example, such data is transmitted when the feeding regimen of the animal is planned.

In one embodiment where the data is implanted on a microchip on a particular animal, the farmer can optimize the efficiency of managing the herd because the farmer is able to identify the genetic predispositions of an individual animal as well as past, present and future treatments (e.g., vaccinations and veterinarian visits). The invention, therefore also provides for accessing other databases, e.g., herd data relating to genetic tests and data performed by others, by datalinks to other sites. Therefore, data from other databases can be transmitted to the central database of the present invention via a network interface for receiving data from the data analysis module of the other databases.

The invention relates to a computer system and a computer readable media for compiling data on an animal, the system containing inputted data on that animal, such as but not limited to, vaccination and medication histories, DNA testing, thyroglobulin testing, leptin, MMI (Meta Morphix Inc.), bovine spongiform encephalopathy (BSE) diagnosis, brucellosis vaccination, FMD (foot and mouth disease) vaccination, BVD (bovine viral diarrhea) vaccination, Sure Health preconditioning program, estrus and pregnancy results, tuberculosis, hormone levels, food safety/contamination, somatic cell counts, mastitis occurrence, diagnostic test results, milk protein levels, milk fat, vaccine status, health records, mineral levels, trace mineral levels, herd performance, and the like. The data of the animal can also include prior treatments as well as suggested tailored treatment depending on the genetic predisposition of that animal toward a particular disease.

The invention also provides for a computer-assisted method for improving animal production comprising using a computer system, e.g., a programmed computer comprising a processor, a data storage system, an input device and an output device, the steps of inputting into the programmed computer through the input device data comprising a breeding, veterinary, medication, diagnostic data and the like of an animal, correlating a physical characteristic predicted by the genotype using the processor and the data storage system, outputting to the output device the physical characteristic correlated to the genotype, and feeding the animal a diet based upon the physical characteristic, thereby improving livestock production.

The invention further provides for a computer-assisted method for optimizing efficiency of feedlots for livestock comprising using a computer system, e.g., a programmed computer comprising a processor, a data storage system, an input device and an output device, and the steps of inputting into the programmed computer through the input device data comprising a breeding, veterinary history of an animal, correlating the breeding, veterinary histories using the processor and the data storage system, outputting to the output device the physical characteristic correlated to the genotype, and feeding the animal a diet based upon the physical characteristic, thereby optimizing efficiency of feedlots for livestock.

The invention further comprehends methods of doing business by providing access to such computer readable media and/or computer systems and/or data collected from animals to users; e.g., the media and/or sequence data can be accessible to a user, for instance on a subscription basis, via the Internet or a global communication/computer network; or, the computer system can be available to a user, on a subscription basis.

In one embodiment, the invention provides for a computer system for managing livestock comprising physical characteristics and databases corresponding to one or more animals.

In another embodiment, the invention provides for computer readable media for managing livestock comprising physical characteristics and veterinary histories corresponding to one or more animals. The invention further provides methods of doing business for managing livestock comprising providing to a user the computer system and media described above or physical characteristics and veterinary histories corresponding to one or more animals. The invention further encompasses methods of transmitting information obtained in any method or step thereof described herein or any information described herein, e.g., via telecommunications, telephone, mass communications, mass media, presentations, internet, email, etc.

The invention further encompasses kits useful for screening nucleic acid isolated from one or more bovine individuals for allelic variation of any one of the FABP genes, and in particular for any of the SNPs described herein, wherein the kits may comprise at least one oligonucleotide selectively hybridizing to a nucleic acid comprising any one of the one or more of which are FABP sequences described herein and instructions for using the oligonucleotide to detect variation in the nucleotide corresponding to the SNP of the isolated nucleic acid.

One embodiment of this aspect of the invention provides an an oligonucleotide that specifically hybridizes to the isolated nucleic acid molecule of this aspect of the invention, and wherein the oligonucleotide hybridizes to a portion of the isolated nucleic acid molecule comprising any one of the polymorphic sites in the FABP sequences described herein.

Another embodiment of the invention is an oligonucleotide that specifically hybridizes under high stringency conditions to any one of the polymorphic sites of the FABP genes, wherein the oligonucleotide is between about 18 nucleotides and about 50 nucleotides.

In another embodiment of the invention, the oligonucleotide comprises a central nucleotide specifically hybridizing with a FABP4 gene polymorphic site of the portion of the nucleic acid molecule.

Another aspect of the invention is a method of identifying a FABP4 polymorphism in a nucleic acid sample comprising isolating a nucleic acid molecule encoding FABP or a fragment thereof and determining the nucleotide at the polymorphic site.

Another aspect of the invention is a method of screening cattle to determine those bovines more likely to exhibit a biological difference in meat quality comprising the steps of obtaining a sample of genetic material from a bovine; and assaying for the presence of a genotype in the bovine which is associated with meat quality, the genotype characterized by a polymorphism in any one of the FABP genes.

In other embodiments of this aspect of the invention, the step of assaying is selected from the group consisting of: restriction fragment length polymorphism (RFLP) analysis, minisequencing, MALD-TOF, SINE, heteroduplex analysis, single strand conformational polymorphism (SSCP), denaturing gradient gel electrophoresis (DGGE) and temperature gradient gel electrophoresis (TGGE).

In various embodiments of the invention, the method may further comprise the step of amplifying a region of the FABP gene or a portion thereof that contains the polymorphism. In other embodiments of the invention, the amplification may include the step of selecting a forward and a reverse sequence primer capable of amplifying a region of the FABP gene.

Another aspect of the invention is a computer-assisted method for predicting which livestock animals possess a biological difference in meat quality comprising: using a computer system, e.g., a programmed computer comprising a processor, a data storage system, an input device and an output device, the steps of: (a) inputting into the programmed computer through the input device data comprising a FABP genotype of an animal, (b) correlating a growth, feed intake, efficiency or carcass merit quality predicted by the FABP genotype using the processor and the data storage system and (c) outputting to the output device the meat quality correlated to the FABP genotype, thereby predicting which livestock animals possess a particular growth, feed intake, efficiency or carcass merit quality.

Yet another aspect of the invention is a method of doing business for managing livestock comprising providing to a user computer system for managing livestock comprising physical characteristics and genotypes corresponding to one or more animals or a computer readable media for managing livestock comprising physical characteristics and genotypes corresponding to one or more animals or physical characteristics and genotypes corresponding to one or more animals.

The invention will now be further described by way of the following non-limiting examples.

EXAMPLES

Example 1

This Example demonstrates that the bovine fatty acid binding protein 4 (FABP4) gene is significantly associated with marbling and subcutaneous fat depth in Wagyu×Limousin $F_2$ crosses.

Evidence has shown that the fatty acid binding protein 4 (FABP4), expressed in adipose tissue interacts with peroxisome proliferator-activated receptors and binds to hormone-sensitive lipase, thus playing an important role in lipid metabolism and homeostasis in adipocytes. The objective of this study was, therefore, to investigate associations of the bovine FABP4 gene with fat deposition in Waygu×Limousin $F_2$ crosses. Both cDNA (625 bp) and genomic DNA (8031bp) sequences of the bovine FABP4 gene were retrieved from the public databases and aligned to determine its genomic organization. Two pairs of primers were designed, which target two regions of the gene, one from bases 5433 to 6106 and one from bases 7417-7868 (SEQ ID NO: 1). Direct sequencing of PCR products on two DNA pools from high/low marbling animals revealed two G/C substitutions at positions 7516 and 7713, respectively. The former G/C substitution can be revealed by PCR-RFLP using restriction enzyme MspA1I and was genotyped on 246 $F_2$ animals in the reference population. Statistical analysis showed that genotype of bovine FABP4 gene significantly affected intramuscular and subcutaneous fat deposition, as indicated by marbling score (P=0.0321) and subcutaneous fat depth (P=0.0246), respectively. The FABP4 gene falls into a suggestive/significant QTL interval for beef marbling reported previously on bovine chromosome 14 in three other populations, which can be immediately implemented in beef breeding programs.

Fatty acid binding proteins are a family of small, highly conserved, cytoplasmic proteins that bind long-chain fatty acids and other hydrophobic ligands (Kaikaus et al. 1990). Their major functions include fatty acid uptake, transport, and metabolism. So far, nine distinct members have been identified in this gene family (Damcott et al. 2004), including adipocyte fatty acid binding protein or fatty acid binding protein 4 (FABP4). FABP4 plays a major role in the regulation of lipid and glucose homeostasis through its interaction with perioxisome proliferator-activated receptors (PPARs), located in the cell nucleus. Specifically, the FABP4/fatty acid complex activates the PPAR-γisoform, which in turn, regulates transcription of FABP4 (Damcott et al. 2004). In addition, FABP4 appears to be involved in lipid hydrolysis and intracellular fatty acid trafficking through direct interaction and binding to hormone-sensitive lipase (Shen et al. 1999), which is a primary enzyme involved in lipid catabolism (Tansey et al. 2003). Recently, FABP4 and FABP5 were proposed as potential candidate genes for obesity as they are located within a quantitative trait loci (QTL) region for serum leptin levels in mice (Ogino et al. 2003). Leptin, a 16-kDa protein secreted from white adipocytes, is involved in the regulation of food intake, energy expenditure, and whole-body energy balance (Jiang et al. 1999). All these factors indicate that FABP4 plays an important role in lipid metabolism and homeostasis in adipocytes. Here, the development of genetic markers in the bovine FABP4 gene and significant association of the gene with marbling and subcutaneous fat depth (SFD) in Wagyu×Limousin $F_2$ crosses is reported.

The genomic sequence of the bovine FABP4 gene has not been described. However, the cDNA sequence of the bovine FABP4 gene (X89244), derived from the bovine mammary gland, was reported previously (Specht et al. 1996). Therefore, a BLAST search was performed using this cDNA sequence as a query to search for its genomic DNA sequence against the 3×bovine genome sequences that have been released to the public domain. These bovine genome sequences can be found, for example, at the Baylor College of Medicine Bovine Genome Project web pages. The process retrieved Bos taurus contig136721 (GenBank accession number AAFC01136716, which is reverse complement with respect to SEQ ID NO:1) that contains the 8,031 bp bovine FABP4 gene sequence. The overall structure of the bovine FABP4 gene was then determined by comparing the genomic DNA sequence with the complete cDNA sequence (FIG. 1). The genomic organization of the bovine FABP4 gene consists of four exons and three introns (FIG. 1), which is comparable to the gene structure in other members of the fatty acid binding protein family and is identical to the same gene structure in human (NC_000008), pig (Y16039), mouse (NC_000069), rat (NC_005101) and chicken (NC_006089). The cDNA—genomic DNA alignment of the bovine FABP4 gene showed 99% sequence identity in one aligned bock (Exon 3, FIG. 1) and 100% sequence identity in three blocks. These four aligned blocks represent the 5' UTR (untranslated region), 4 exons and the 3' UTR. Therefore, this 8,031 bp genomic sequence of the bovine FABP4 could be tentatively partitioned into the following organizational parts: 1,819 bp for proximal promoter, 67 bp for 5' UTR of exon 1, 66 bp for CDS of exon 1, 2,709 bp for intron 1, 173 bp for exon 2, 594 bp for intron 2, 102 bp for exon 3, 463 bp for intron 3, 51 bp for CDS of exon 4, 169 bp for 3' UTR of exon 4 and 1,887 bp for 3' untranscribed sequence, respectively (FIG. 1).

A Wagyu×Limousin reference population was developed jointly by Washington State University and the Fort Keogh Livestock and Range Research Laboratory, ARS, USDA. The $F_1$ crosses, including 6 $F_1$ bulls and 113 dams, were generated at Washington State University and transferred to the USDA research station in the autumn of 1998. Inter se mating of these $F_1$ animals produced 71 $F_2$ progeny in 2000, 90 in 2001 and 109 in 2002, respectively. Growth rate, carcass and meat quality data, including marbling scores and SFD, were collected on all $F_2$ calves. Marbling score is a subjective measure of the amount of intramuscular fat in the longissimus muscle based on USDA standards (http://www.ams.usda.gov/). SFD was measured at the 12-13th rib interface perpendicular to the outside surface at a point three-fourths the length of the longissimus muscle from its chine bone end. Marbling scores varied from 4=Slight[0] to 9.5=Moderately Abundant[50]

(SD=1.00) and SFD measurements ranged from 0.1 to 1.3 inches (SD=0.18) in this $F_2$ population. DNA was extracted from blood samples. Based on the availability of both data and DNA samples, 246 observations were used in the current study. Two DNA pools were formed from the reference population, one from 20 individuals with the highest marbling scores (HMS pool) and one from 20 individuals with the lowest marbling scores (LMS pool), for an initial screening of association of markers with the traits.

Two pairs of primers were designed to detect genetic polymorphisms in the bovine FABP4 gene, based on the genomic contig136721 sequence (GenBank accession number AAFC01136716. Since the genomic contig is 3' to 5' with respect to the 5' to 3' direction of the FABP4 gene, all numbering in this paper is based on the reverse complement of this sequence, which is set forth in SEQ ID NO:1). The first primer pair (forward sequence, 5'TCG TAA ACT TAG ATG AAG GTG CTC TGG 3' (SEQ ID NO: 2) and reverse sequence, 5' ACG TAT CCA GCA GAA AGT CAT GGA G 3' (SEQ ID NO: 3) targets a region from bases 5433 to 6106. This region includes exon 3, intron 3 and exon 4, and a putative G/A substitution was found in exon 3 based on sequence alignment between the cDNA and genomic DNA of the bovine FABP4 gene. The second primer pair (forward sequence, 5' ATA TAG TCC ATA GGG TGG CAA AGA 3' (SEQ ID NO: 4) and reverse sequence, 5' AAC CTC TCT TTG AAT TCT CCA TTC T 3' (SEQ ID NO: 5) amplifies a region of 7417-7868 bp, which contains a short tandem repeat of "CA". Approximately 50 ng of genomic DNA from the HMS and LMS pools was amplified in a final volume of 10 µL that contained 12.5 ng of each primer, 150 µM dNTPs, 1.5 mM $MgCl_2$, 50 mM KCl, 20 mM Tris-HCl and 0.25 U of Platinum Taq polymerase (Invitrogen, Carlsbad, Calif.). The PCR conditions were carried out as follows: 94° C. for 2 min, 32 cycles of 94° C. for 30 sec, 63° C. (for the first primer pair) or 56° C. (for the second primer pair) for 30 sec and 72° C. for 30 sec, followed by a further 5 min extension at 72° C. PCR products were examined by electrophoresis through a 1.5% agarose gel with 1× TBE buffer to determine the quality and quantity of DNA for sequencing.

Figure 3:
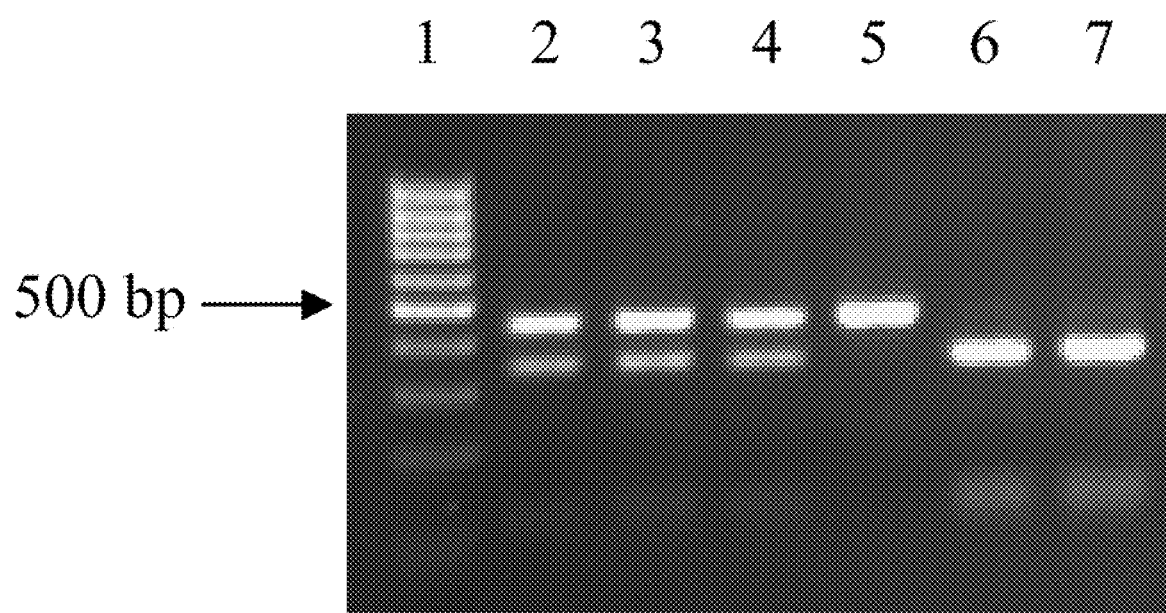
FIG. 3 depicts PCR-RFLP genotyping of the C/G substitution at position 7516 of the bovine FABP4 gene. Lane 1: 100 bp ladder. Lanes 2-7: a 452 bp amplicon was digested with the restriction enzyme MspA1I. Lanes 2-4, CG animals show 3 bands after complete digestion, 452, 352 and 100 bp; Lane 5, CC animals do not have an MspA1I site and the 452 bp amplicon is not digested; Lanes 6 and 7, GG animals have one MspA1I site and reveal after complete digestion two bands: 352 bp and 100 bp.

Direct sequencing of PCR products from two DNA pools was performed on ABI 3730 sequencer in the Laboratory for Biotechnology and Bioanalysis (Washington State University) using a standard protocol. However, DNA sequencing did not confirm the existence of a G/A substitution in exon 3 or a variation in the number of CA repeats in the 3' untranscribed region of the bovine FABP4 gene between HMS and LMS pools. Instead, two single nucleotide polymorphisms (SNPs) were detected in the products amplified with the second primer pair, including a G/C substitution located at position 7516 (FIG. 2A) and a G/C substitution at 7713 bp within the CA repeat region (FIG. 2B). Restriction map analysis indicated that the G/C substitution at 7516 bp could be genotyped by PCR-RFLP using restriction enzyme MspA1I. This G/C SNP in the bovine FABP4 gene was then individually genotyped in DNA from Wagyu×Limousin $F_2$ animals with recorded marbling scores and SFD measurements. After PCR amplification, the amplicons were digested at 37° C for three hours with 2U of MspA1I (New England Biolabs, Beverly, Mass.) followed by analysis on 1.5% agarose gels. The 452 bp amplicon with the C/G substitution at 7516 bp contains a single polymorphic site for the restriction enzyme MspA1I. Therefore, GG homozygous animals have one MspA1I site and reveal after complete digestion two bands: 100 bp and 352 bp. In comparison, homozygous animals with C allele have lost the MspA1I recognition site at this position and show only the 452 bp band. Heterozygous animals are identified by the presence of three bands after MspA1I digestion (FIG. 3). Of the 232 animals genotyped, 139 were homozygotes with allele C, 21 were homozygotes with allele G, and the remaining 72 were heterozygotes with both alleles C and G (Table 1). The genotype distribution was in Hardy-Weinberg equilibrium ($\chi^2$=2.82, P>0.05).

TABLE 1

Associations of the bovine FABP4 G/C SNP at position 7516 with marbling and SFD in Waygu × Limousin F2 crosses.

| Genotype | No. of animals | Marbling (score) Mean ± S.E. | P value | SFD (in inch) Mean ± S.E. | P value |
|---|---|---|---|---|---|
| CC | 139 | −0.164 ± 0.086$^a$ | 0.0321 | −0.026 ± 0.013$^a$ | 0.0246 |
| GC | 72 | 0.160 ± 0.119$^b$ | | 0.031 ± 0.017$^b$ | |
| GG | 21 | 0.265 ± 0.221$^{ab}$ | | 0.016 ± 0.018$^{ab}$ | |

$^{ab}$Means within a row without common superscripts are significantly different (P < 0.05).

The phenotypic data for marbling scores and SFD measurements were analyzed using the GLM (general linear model) procedure of SAS v9.1 (SAS institute Inc., Gary, N.C.). The fixed effects of the model included year of birth, gender, age at harvest (linear) and the genotype for a G/C substitution at 7516 bp of the FABP4 gene. Pairwise comparisons of least-squares means were performed using a protected t-test. Genotype significantly affected intramuscular and subcutaneous fat deposition (Table 1), as indicated by marbling score (P=0.0321) and SFD (P=0.0246), respectively. Because the number of animals with the GG genotype was relatively low in the population, significant differences in SFD or marbling scores were not detected. However, numerically, animals homozygous with the G allele had greater SFD and higher marbling scores than animals homozygous with the C allele. Animals with the heterozygous genotype had significantly greater (P<0.05) marbling scores and SFD than animals with the CC genotype. While these results are the first known report of an association between FABP4 genotype and either marbling score or SFD in cattle, other researchers have reported significant polymorphisms in the porcine FABP4 gene that were related to lipid accretion. Gerbens et al. (1998) detected a microsatellite marker in the porcine FABP4 gene that was polymorphic in six pig breeds. Genotypes for this microsatellite were significantly associated with the intramuscular fat content of the longissimus dorsi muscle of Duroc pigs (Gerbens et al. 1998) and longissimus lumborum muscle biopsies of crossbred barrows (Gerbens et al. 2001). In addition, Ye and coworkers (2002) indicated that a BsmI locus in the porcine FABP4 gene near the microsatellite marker described by Gerbens et al. (1998) was significantly associated with intramuscular fat content.

Several reports have demonstrated that bovine chromosome 14 (BTA14) harbors significant or suggestive QTL for marbling (intramuscular fat content) and SFD in beef cattle. Casas and colleagues (2003) reported a suggested QTL for marbling in a Bos indicus×Bos taurus family located at 47 cM and a suggested QTL for SFD at 16 cM on BTA14. Taylor and Schnabel (2004) (http://animalgenomics.missouri.edu/) recently developed a DNA repository from the semen of 1600 registered bulls representing 14 generations of the American Angus Association for an Angus Genome project and confirmed the existence of a marbling QTL with a similar location as the QTL identified by Casas and colleagues (2003). In purebred Japanese black cattle, a QTL for marbling was found in the centromeric regions of BTA14 (Imai et al. 2004). Standardization of these marker locations based on the newest version of bovine linkage map (Ihara et al. 2004) demonstrated these QTLs span an interval between 59 cM and 70 cM on BTA14. Integration of both genetic map (Ihara et al. 2004) and RH map (Itoh et al. 2005) of BTA14 predicted that the FABP4 gene should be placed somewhere between 63.156 and 63.859 cM on the linkage map of the bovine chromosome. These data indicate that the FABP4 gene falls into a QTL interval for marbling reported in three different populations as described above. References:

Casas et al. 2003. Detection of quantitative trait loci for growth and carcass composition in cattle. J Anim Sci. 81: 2976-2983.

Damcott et al. 2004. Metabolism, 53: 303-309.

De et al. 2004. Proceedings, Western Section, American Society of Animal Science, 55: 95-98.

Gerbens et al. 2001. J Anim Sci. 79: 347-354.

Gerbens et al. 1998. Mamm Genome, 9: 1022-1026.

Ihara et al. 2004. Genome Res. 14: 1987-1998.

Imai et al. 2004. Proceedings of the 29th International Conference on Animal Genetics, Tokyo, Japan. p.118.

Itoh et al. 2005. Genomics, 85: 413-424.

Jiang and Gibson 1999. Mamm Genome, 10: 191-193.

Kaikaus et al. 1990. Experientia, 46: 617-630.

Shen et al. 1999. Proc Natl Acad Sci U S A, 96: 5528-5532.

Specht et al. 1996. J Biol Chem. 271: 19943-19949.

Tansey et al. 2003. J Biol Chem. 278: 8401-8406.

Thaller et al. 2003. Anim Genet. 34: 354-357.

Ye et al. 2002. 7th World Congress on Genetics Applied to Livestock Production, Montpellier, France, 31: 359-362.

Example 2

This Example provides associations between TFAM-1, TFAM-2, and FABP4 markers and carcass traits in commercial feedlot steers and heifers.

The following markers were evaluated: (1) a C to A substitution at the 1220 nucleotide position in the mitochondrial transcription factor A gene (TFAM-1) promoter, (2) a C to T substitution at the 1212 nucleotide position in the TFAM-2 promoter and (3) a G to C substitution at the 7516 nucleotide position of the fatty acid binding protein 4 gene (FABP4). Previous results indicate that the markers affect Markers affect marbling and backfat.

Initially, there were 1,589 records initially from steers and heifers. The target endpoint was 12.2 mm backfat. Harvest date was predicted optimal economic endpoint by animal. Contemporary groups included source and sex. It was assumed that the breed type confounded with the source. The final data set included the number of records based on available phenotypes and genotypes for each trait.

The tested traits are: hot carcass weight (HCW, lb), ribeye area (REA, in$^2$), ribeye area per hundred weight HCW (REA/cwt HCW, in$^2$/100 lb hot carcass weight (HCW), hot carcass weight value (HCW value, $), calculated live weight (Calc Lv Wt, lb), dry matter intake (DMI, lb), days on feed (DOF, d), dry matter intake per day on feed (DMI per DOF, lb/d), average daily gain (ADG, lb/d), dressing percentage (DP, %), backfat thickness (BFAT, in), calculated yield grade (cYG), quality grade, less than or equal to select versus greater than or equal to choice (QG, <Se vs, >Ch), intramuscular fat content (IMF%, %), marbling score (MBS, 10 to 99), marbling score divided by days on feed (MBS/DOF), additional carcass value (additional carc value, $), adjusted net return—all costs removed (adj. net return—all costs removed, $) and adjusted net return—initial animal value not removed (adj. net return—initial animal value not removed, $).

The analysis models were genotype, wherein genotypes were fit as fixed effects and additive or allele substitution, which showed regression on allele number (0, 1, 2). Both models fit with 2-marker combinations. Another analysis model is haplotype, which shows regression on (expected) haplotype when fitting multiple TFAM markers. Significant single marker associations are presented in Table 2 and significant 2-marker combinations are presented in Table 3.

TABLE 2

Single Marker Analyses for TFAM-1, TFAM-2, & FABP4

| | | | Model | | | | | | | |
|---|---|---|---|---|---|---|---|---|---|---|
| | | | Allele Substitution | | | Fixed genotype | | | Genotype | | |
| | | | | | | | | | Add. | | Dom. |
| Marker | Trait | N | Estimate | SE | P-value | P-value | Add. est. | SE | P-Value | Dom. est. | SE | P-value |
| FABP4 | QG Ch(1, 2, 5, 9, 20) | 1528 | −.065 | .019 | .0007 | .0027 | −.057 | .023 | .0156 | .020 | .030 | .5161 |
| | REA/cwt HCW | 1528 | .00016 | .00009 | .0558 | .0345 | .00027 | .00010 | .0102 | .00023 | .00013 | .0795 |
| TFAM-1 | Calc Lv Wt | 1539 | 10.629 | 3.578 | .0030 | .0122 | 10.794 | 3.731 | .0039 | .816 | 5.178 | .8748 |
| | Hot Carcass Wt | 1539 | 5.929 | 2.402 | .0137 | .0478 | 5.894 | 2.504 | .0187 | −.172 | 3.476 | .9606 |
| | HCW Value | 1539 | .274 | .192 | .1535 | .0073 | .432 | .200 | .0308 | .776 | .277 | .0052 |
| | Marbling score | 1125 | .906 | .358 | .0115 | .0354 | .962 | .373 | .0099 | .281 | .516 | .5865 |
| | MBS/DOF | 1125 | .006 | .003 | .0452 | .0892 | .007 | .003 | .0296 | .004 | .004 | .3641 |
| TFAM-2 | Calc Lv Wt | 1503 | −9.607 | 3.590 | .0075 | .0099 | −10.145 | 3.608 | .0050 | −7.321 | 5.070 | .1490 |
| | Hot Carcass Wt | 1503 | −5.931 | 2.418 | .0143 | .0270 | −6.208 | 2.431 | .0107 | −3.775 | 3.416 | .2693 |
| | HCW Value | 1503 | −.453 | .193 | .0191 | .0104 | −.415 | .194 | .0326 | .520 | .273 | .0567 |
| | Marbling score | 1097 | −.845 | .366 | .0210 | .0557 | −.872 | .368 | .0179 | −.345 | .512 | .5005 |
| | Ribeye Area | 1503 | −.142 | .058 | .0139 | .0439 | −.139 | .058 | .0165 | .037 | .082 | .6503 |

Markers fit for allele substitution: A for TFAM1; C for TFAM2 & FABP4

Marbling scores range from 10 to 99; 10 = PD0 = Std, 99 = A90 = Prime

QG Ch(1, 2, 5, 9, 20) implies Ch or better - includes Prime, Ch, CAB, Sterling Silver, & Angus Pride;

Alternate included Se, No Roll, Dark cutter, & Hard bone

TABLE 3

Two Marker Analyses for TFAM-1, TFAM-2, & FABP4

| | | | | Model Allele Substitution | | | | | |
|---|---|---|---|---|---|---|---|---|---|
| | | | | Marker 1 | | | Marker 2 | | |
| Marker 1 | Marker 2 | Trait | N | Estimate | SE | P-value | Estimate | SE | P-value |
| TFAM-1 | FABP4 | Adj NR w/o init val | 1526 | −1.383 | 4.007 | .7300 | −.416 | 3.786 | .9124 |
| | | Calc Lv Wt | 1526 | 12.076 | 4.388 | .0060 | −4.194 | 4.146 | .3119 |
| | | Hot Carcass Wt | 1526 | 7.092 | 2.948 | .0163 | −2.672 | 2.785 | .3374 |
| | | IMF % | 377 | −.046 | .078 | .5526 | −.056 | .072 | .4345 |
| | | MBS/DOF | 1117 | .007 | .003 | .0299 | −.001 | .003 | .8048 |
| | | Marbling score | 1117 | 1.069 | .429 | .0128 | −.334 | .408 | .4140 |
| | | QG Ch(1, 2, 5, 9, 20) | 1526 | −.004 | .021 | .8403 | −.072 | .020 | .0003 |
| TFAM-1 | TFAM-2 | Adj NR w/o init val | 1501 | 8.151 | 5.602 | .1459 | 11.913 | 5.791 | .0398 |
| | | DMI | 1501 | 22.819 | 25.853 | .3776 | −2.520 | 26.725 | .9249 |
| | | DMI/DOF | 1501 | .208 | .179 | .2457 | .034 | .185 | .8555 |
| | | HCW Value | 1501 | −.466 | .328 | .1561 | −.938 | .339 | .0058 |
| | | QG Ch(1, 2, 5, 9, 20) | 1501 | −.042 | .030 | .1558 | −.066 | .031 | .0302 |
| | | YG | 1434 | .080 | .039 | .0419 | .059 | .041 | .1481 |
| TFAM-2 | FABP4 | Calc Lv Wt | 1495 | −11.350 | 4.367 | .0094 | −5.556 | 4.050 | .1703 |
| | | DOF | 1495 | −.181 | .475 | .7030 | −.672 | .441 | .1274 |
| | | Hot Carcass Wt | 1495 | −6.424 | 2.943 | .0292 | −3.431 | 2.729 | .2090 |
| | | Marbling score | 1093 | −.990 | .433 | .0223 | −.372 | .403 | .3568 |
| | | QG Ch(1, 2, 5, 9, 20) | 1495 | −.017 | .021 | .4248 | −.063 | .020 | .0014 |
| | | REA/cwt HCW | 1495 | −.00002 | .00009 | .8546 | .00018 | .00009 | .0385 |

| | | | Model Genotype | | | | | |
|---|---|---|---|---|---|---|---|---|
| | | | Markers 1*2 | | | Marker 1 | Marker 2 | Markers 1*2 |
| Marker 1 | Marker 2 | Trait | Estimate | SE | P-value | P-value | P-value | P-value |
| TFAM-1 | FABP4 | Adj NR w/o init val | −.621 | 5.003 | .9013 | .4996 | .2159 | .0404 |
| | | Calc Lv Wt | −3.120 | 5.478 | .5691 | .0153 | .2933 | .6639 |
| | | Hot Carcass Wt | −2.237 | 3.680 | .5435 | .0393 | .1629 | .5571 |
| | | IMF % | .042 | .095 | .6598 | .4765 | .9997 | .0372 |
| | | MBS/DOF | −.004 | .004 | .4059 | .0426 | .8568 | .6798 |
| | | Marbling score | −.317 | .543 | .5594 | .0282 | .4454 | .8402 |
| | | QG Ch(1, 2, 5, 9, 20) | .034 | .026 | .2028 | .6912 | .0016 | .6534 |
| TFAM-1 | TFAM-2 | Adj NR w/o init val | −2.564 | 5.312 | .6294 | .1528 | .0868 | .3998 |
| | | DMI | −12.727 | 24.514 | .6037 | .0152 | .0230 | .0388 |
| | | DMI/DOF | −.022 | .170 | .8989 | .0142 | .0171 | .0479 |
| | | HCW Value | .650 | .311 | .0368 | .3637 | .9102 | .6043 |
| | | QG Ch(1, 2, 5, 9, 20) | .033 | .028 | .2388 | .2871 | .5127 | .2949 |
| | | YG | −.040 | .037 | .2760 | .4031 | .5462 | .7033 |
| TFAM-2 | FABP4 | Calc Lv Wt | 4.329 | 5.306 | .4147 | .0113 | .1017 | .6175 |
| | | DOF | .209 | .577 | .7175 | .9786 | .0189 | .0398 |
| | | Hot Carcass Wt | 1.235 | 3.576 | .7299 | .0530 | .0614 | .8073 |
| | | Marbling score | .311 | .529 | .5568 | .0726 | .8003 | .8134 |
| | | QG Ch(1, 2, 5, 9, 20) | −.025 | .026 | .3308 | .8411 | .0051 | .2986 |
| | | REA/cwt HCW | −.00011 | .00011 | .3377 | .8702 | .0523 | .2467 |

Markers fit for allele substitution: A for TFAM1; C for TFAM2 & FABP4
Marbling scores range from 10 to 99; 10 = PD0 = Std, 99 = A90 = Prime
QG Ch(1, 2, 5, 9, 20) implies Ch or better - includes Prime, Ch, CAB, Sterling Silver, & Angus Pride;
Alternate included Se, No Roll, Dark cutter, & Hard bone Example 3

Figure 5:
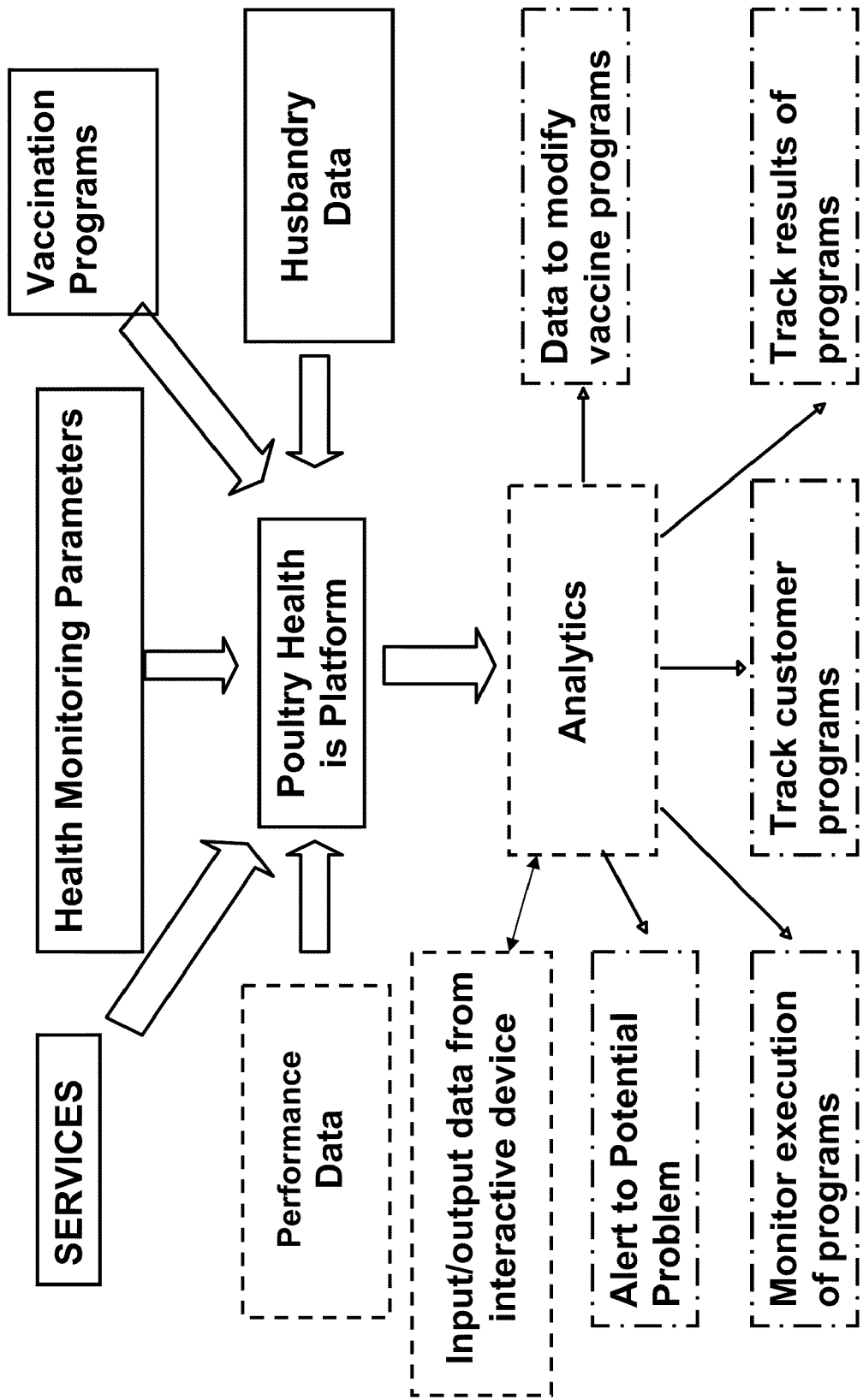
FIG. 5 illustrates a flowchart of the input of data and the output of results from the analysis and correlation of the data pertaining to the breeding, veterinarian histories and performance requirements of a group of animals such as from a herd of cows and the interactive flow of data from the computer-assisted device to a body of students learning the use of the method of the invention.

FIG. 5 shows a flowchart of the input of data and the output of results from the analysis and correlation of the data pertaining to the breeding, veterinarian histories and performance requirements of a group of animals such as from bovines. The flowchart illustrated in FIG. 5 further indicates the interactive flow of data from the computer-assisted device to a body of students learning the use of the method of the invention and the correlation of such interactive data to present an output as a pie-chart indicating the progress of the class. The flowchart further indicates modifications of the method of the invention in accordance with the information received from the students to advance the teaching process or optimize the method to satisfy the needs of the students.

Figure 6:
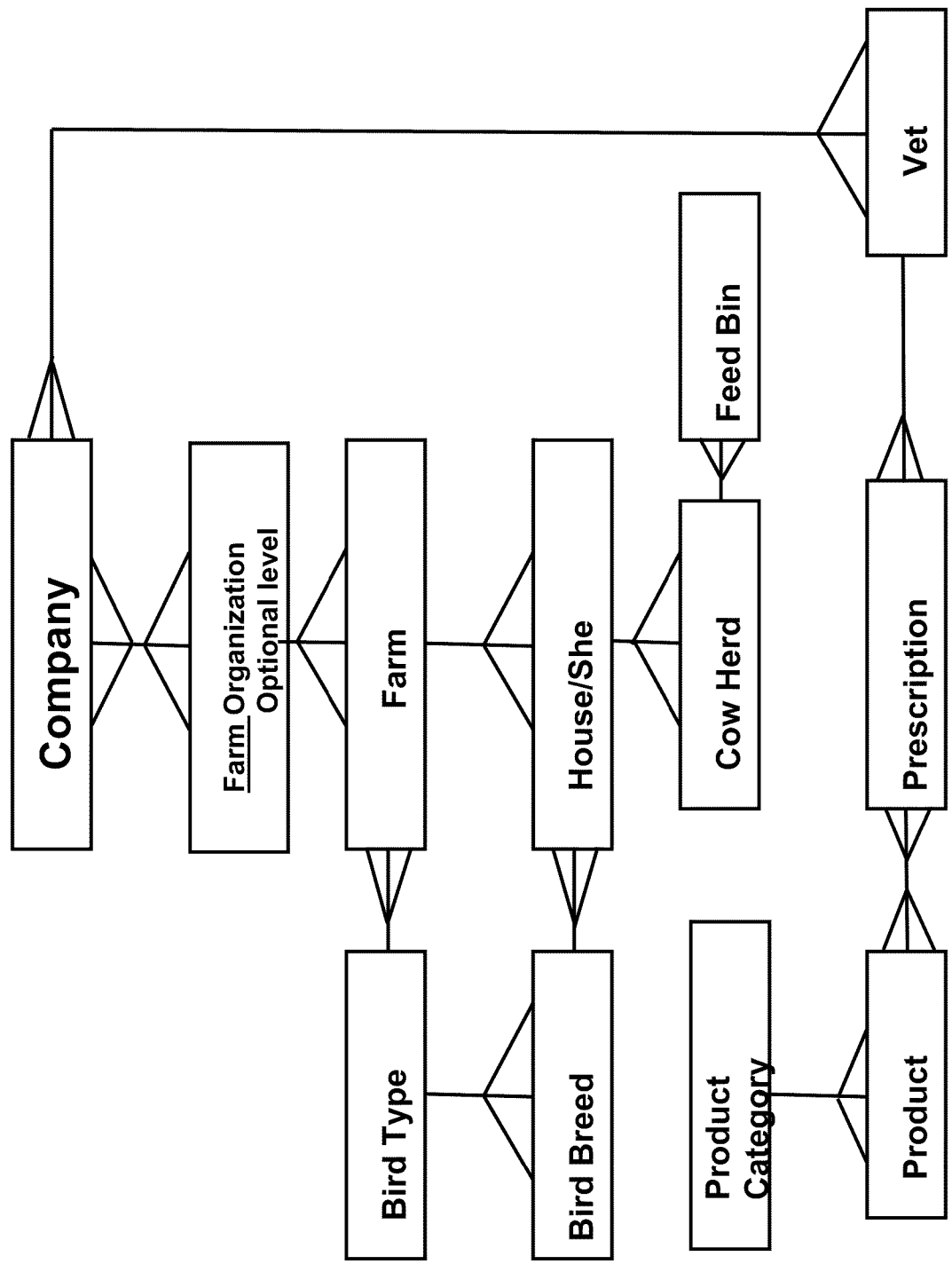
FIG. 6 illustrates potential relationships between the data elements to be entered into the system. Unidirectional arrows indicate, for example, that a barn is typically owned by only one farm, whereas a farm may own several barns. Similarly, a prescription may include veterinarian products.

FIG. 6 illustrates potential relationships between the data elements to be entered into the system. Unidirectional arrows indicate, for example, that a barn is typically owned by only one farm, whereas a farm may own several barns. Similarly, a prescription may include veterinarian products.

Figure 7A:
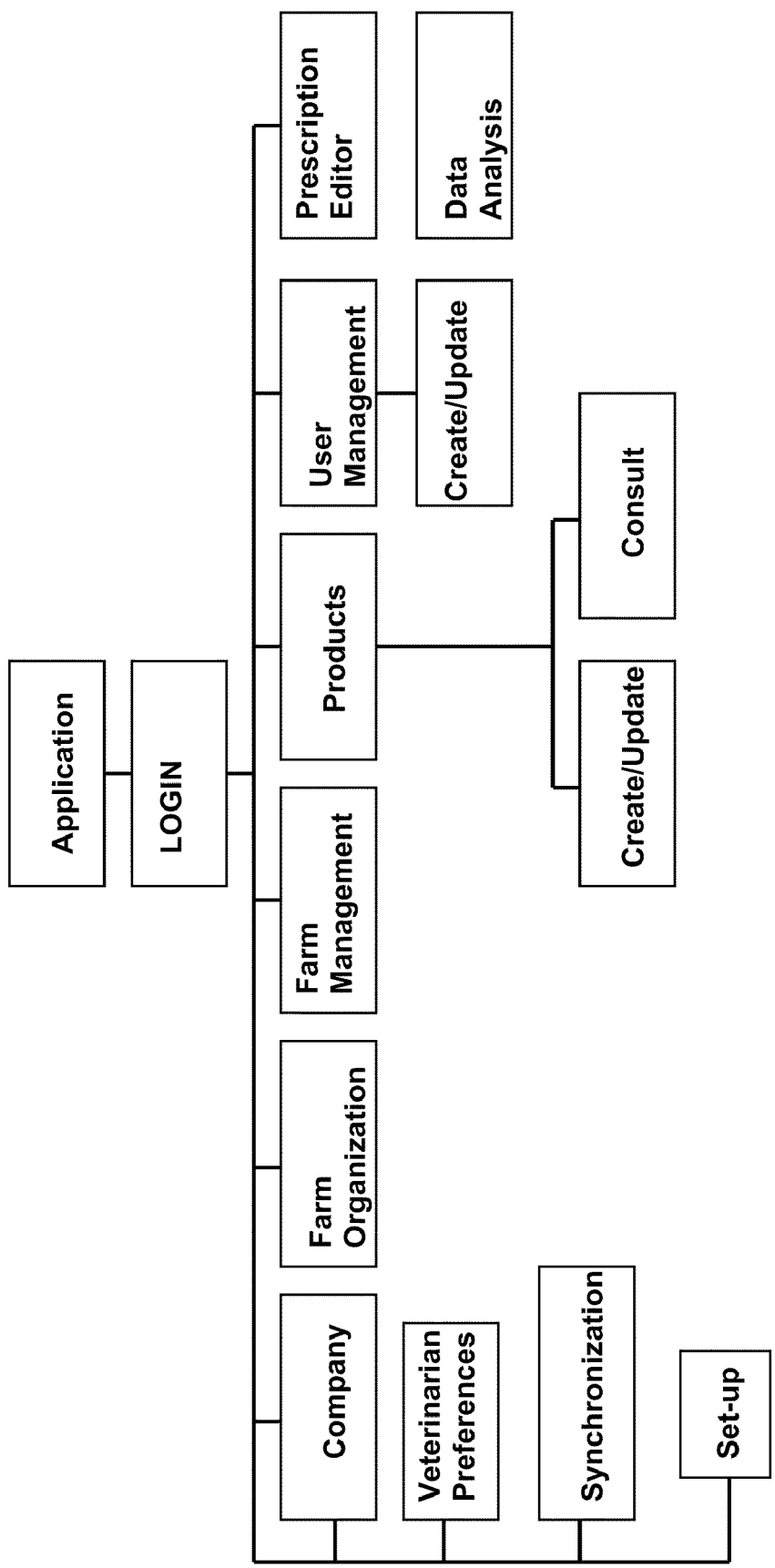
FIG. 7A illustrates the flow of events in the use of the portable computer-based system for data entry on the breeding and rearing of a herd of cows.
Figure 7B:
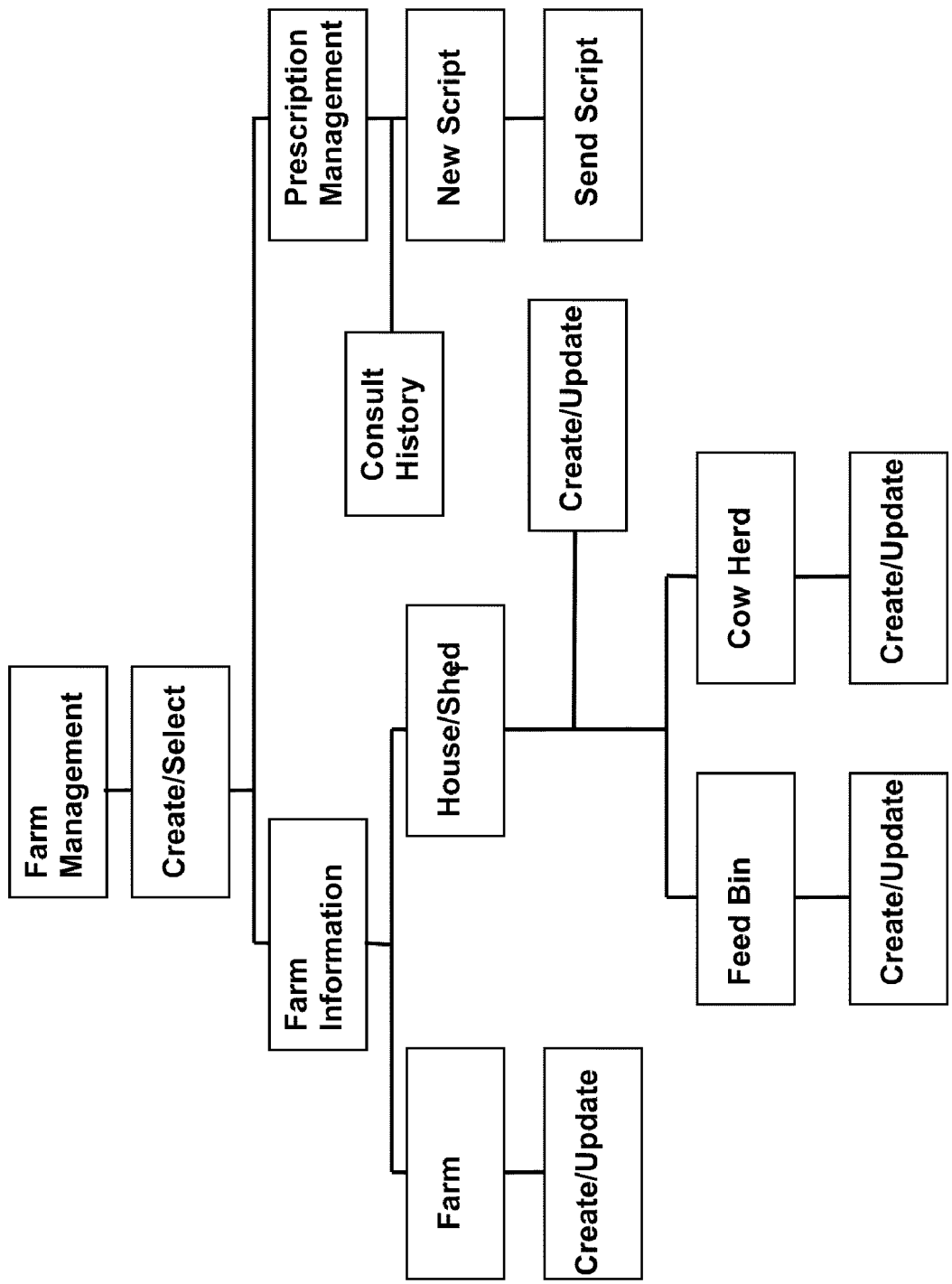
FIG. 7B illustrates the flow of events through the subroutines related to data entry concerning farm management.
Figure 7C:
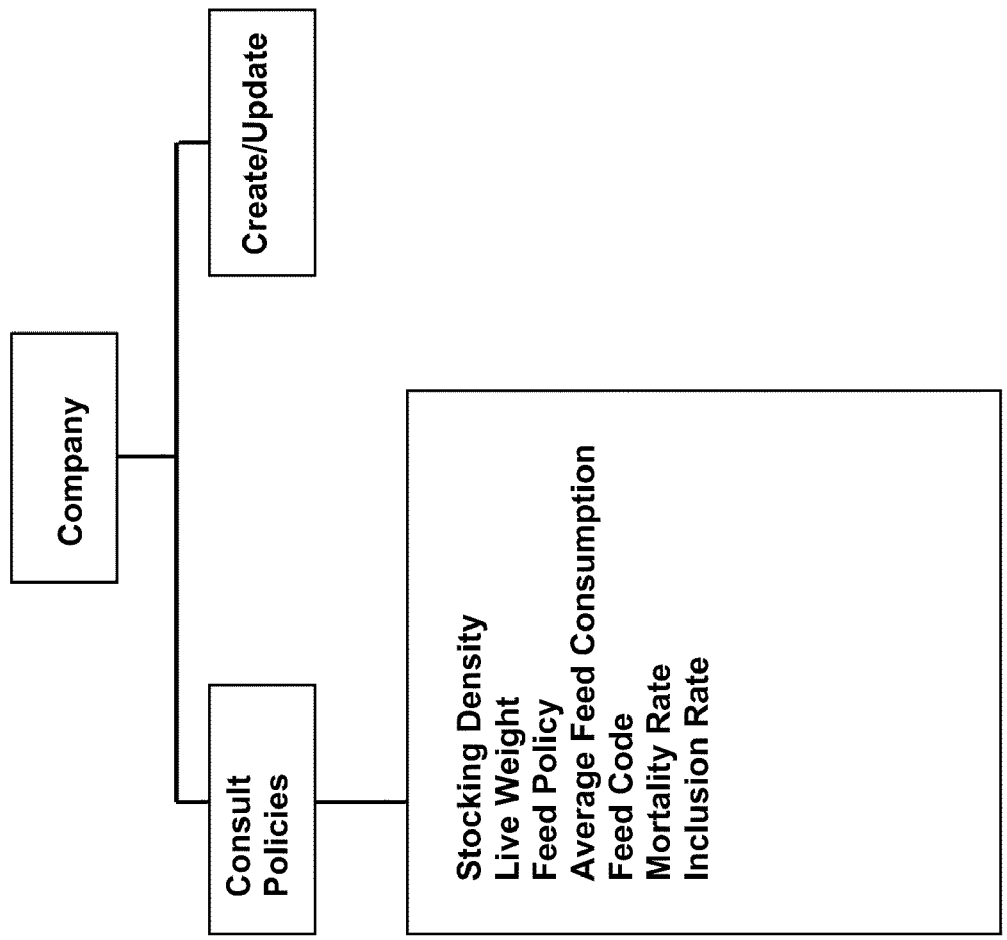
FIG. 7C illustrates the flow of events through the subroutines related to data entry concerning data specific to a company.

FIG. 7A illustrates the flow of events in the use of the portable computer-based system for data entry on the breeding and rearing of a herd of cows. FIG. 7B illustrates the flow of events through the sub-routines related to data entry concerning farm management. FIG. 7C illustrates the flow of events through the sub-routines related to data entry concerning data specific to a company.

Figure 8:
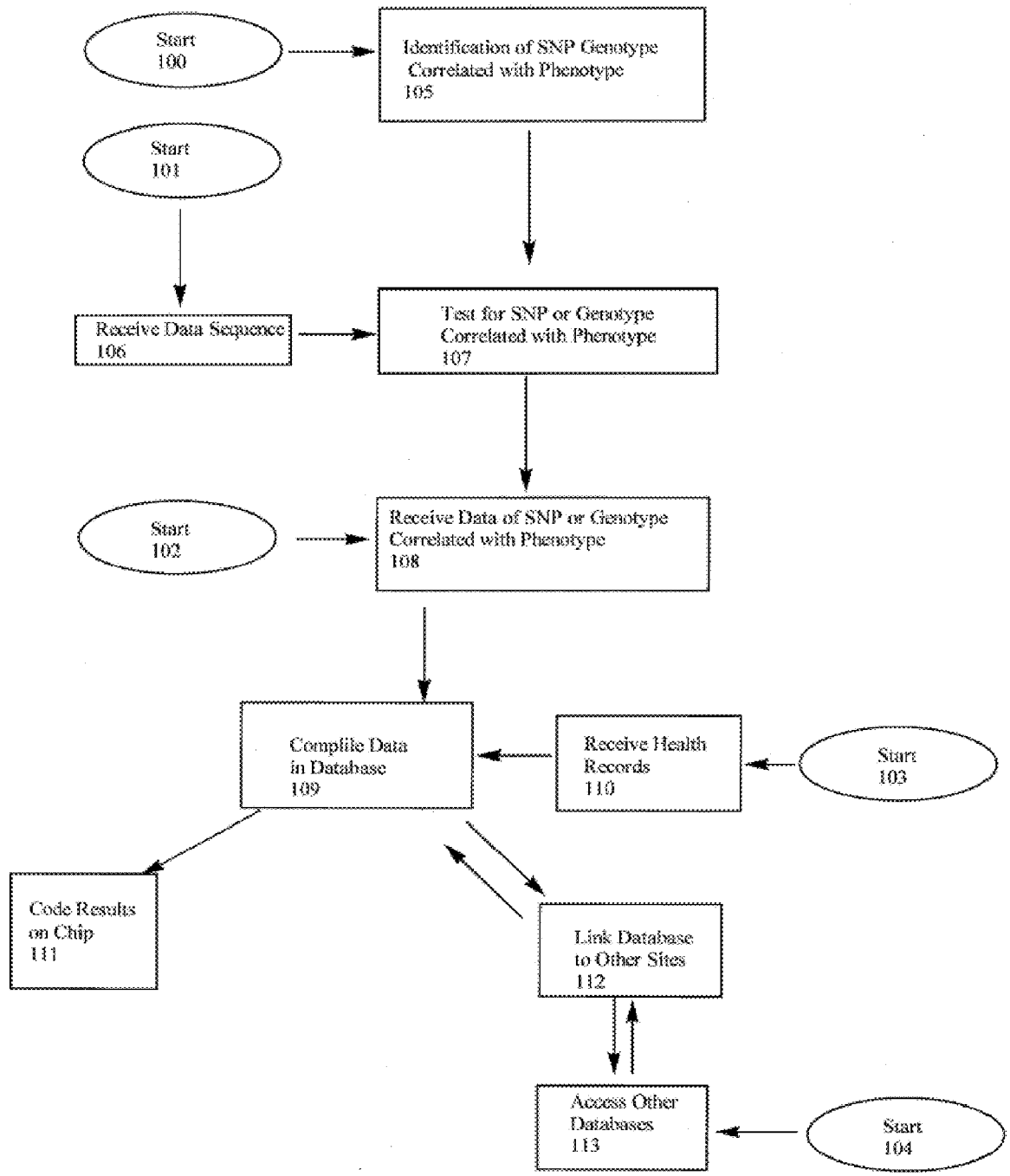
FIG. 8 illustrates a flow chart of the input of data and the output of results from the analysis and the correlation of the data pertaining to the breeding, veterinarian histories, and performance requirements of a group of animals.

FIG. 8 illustrates a flow chart of the input of data and the output of results from the analysis and the correlation of the data pertaining to the breeding, veterinarian histories, and performance requirements of a group of animals.

The invention is further described by the following numbered paragraphs:

1. A method for sub grouping animals according to genotype wherein the animals of each sub-group have a similar polymorphism in a fatty acid binding protein 4 ("FABP4") gene comprising:
   (a) determining the genotype of each animal to be subgrouped by determining the presence of a single nucleotide polymorphism in the FABP4 gene, and
   (b) segregating individual animals into sub-groups wherein each animal in a subgroup has a similar polymorphism in the FABP4 gene.

2. A method for sub grouping animals according to genotype wherein the animals of each sub-group have a similar genotype in the FABP4 gene comprising:
   (a) determining the genotype of each animal to be subgrouped by determining the presence of a single nucleotide polymorphism(s) of interest in the FABP4 gene,
   (b) segregating individual animals into sub-groups depending on whether the animals have, or do not have, the single nucleotide polymorphism(s) of interest in the FABP4 gene.

3. The method of paragraphs 1 or 2, wherein the single nucleotide polymorphism(s) of interest is selected from the group consisting of a G to C substitution at the 7516 nucleotide position of the FABP4 gene and a G to C substitution at position 7713 of the FABP4 gene.

4. A method for sub grouping animals according to genotype wherein the animals of each sub-group have a similar genotype in the FABP4 gene comprising:
   (a) determining the genotype of each animal to be subgrouped by determining the presence of a G to C substitution at the 7516 nucleotide position of the FABP4 gene and a G to C substitution at position 7713 of the FABP4 gene, and
   (b) segregating individual animals into sub-groups depending on whether the animals have, or do not have, G to C substitution at the 7516 nucleotide position of the FABP4 gene and a G to C substitution at position 7713 of the FABP4 gene.

5. A method for identifying an animal having a desirable phenotype as compared to the general population of animals of that species, comprising determining the presence of a single nucleotide polymorphism in the FABP4 gene of the animal, wherein the polymorphism is selected from the group consisting of G to C substitution at the 7516 nucleotide position of the FABP4 gene and a G to C substitution at position 7713 of the FABP4 gene single nucleotide polymorphism is indicative of a desirable phenotype.

6. The method of paragraph 5, wherein the desirable phenotype is feed intake, growth rate, body weight, carcass merit and composition, milk yield or any combination thereof.

7. The method of paragraph 5 or 6, wherein the desirable phenotype is additional carcass value (additional carc value, $), average daily gain (ADG, lb/d), backfat thickness (BFAT, in), calculated live weight (Calc Lv Wt, lb), calculated yield grade (cYG), days on feed (DOF, d), dressing percentage (DP, %), dry matter intake (DMI, lb), dry matter intake per day on feed (DMI per DOF, lb/d), hot carcass weight (HCW, lb), hot carcass weight value (HCW value, $), intramuscular fat content (IMF%, %), marbling score (MBS, 10 to 99), marbling score divided by days on feed (MBS/DOF), quality grade, less-than or equal to select versus greater than or equal to choice (QG, <Se vs, >Ch), ribeye area (REA, in$^2$), ribeye area per hundred weight HCW (REA/cwt HCW, in$^2$/100 lb hot carcass weight (HCW), subcutaneous fat depth (SFD) or any combination thereof.

8. The method of any one of paragraphs 1 to 7 wherein the animal is a bovine.

9. The method of any one of paragraphs 1 to 8 wherein the FABP4 gene is a bovine FABP gene.

10. An interactive computer-assisted method for tracking the rearing of livestock bovines comprising, using a computer system comprising a programmed computer comprising a processor, a data storage system, an input device, an output device, and an interactive device, the steps of: (a) inputting into the programmed computer through the input device data comprising a breeding history of a bovine or herd of bovines, (b) inputting into the programmed computer through the input device data comprising a veterinary history of a bovine or herd of bovines, (c) correlating the veterinary data with the breeding history of the bovine or herd of bovines using the processor and the data storage system, and (d) outputting to the output device the breeding history and the veterinary history of the bovine or herd of bovines.

11. The method according to paragraph 10, wherein the computer system is an interactive system whereby modifications to the output of the computer-assisted method may be correlated according to the input from the interactive device.

12. The method according to paragraph 10 or 11, further comprising the steps of inputting into the programmed computer diagnostic data related to the health of the cow or herd of cows; and correlating the diagnostic data to the breeding and veterinary histories of the cow or herd of cows.

13. The method according to any one of paragraphs 10 to 12, wherein the veterinary data comprises a vaccination record for a cow or herd of cows.

14. The method according to any one of paragraphs 10 to 13 wherein the health data is selected from the group consisting of husbandry condition data, herd history, and food safety data.

15. The method according to any one of paragraphs 10 to 14, further comprising at least one further step selected from the group consisting of inputting into the programmed computer data related to the quality control of the bovine or herd of bovines and correlating the quality control data to the breeding and veterinary histories of the cow or herd of cows, inputting into the programmed computer performance parameters of the cow or herd of cows; and correlating the required performance parameters of the bovine or herd of bovines to a specific performance requirement of a customer, correlating the vaccine data to the performance parameters of the bovine or herd of bovines, correlating herd to the performance parameters of the bovine or herd of bovines, correlating the food safety data to the performance parameters of the bovine or herd of bovines, correlating the husbandry condition data to the performance parameters of the bovine or herd of bovines, inputting into the programmed computer data related to the nutritional data of the bovine or herd of bovines; and correlating the nutritional data to the performance parameters of the bovine or herd of bovines, and alerting to undesirable changes in the performance parameters of the bovine or herd of bovines.

16. The method according to any one of paragraphs 10 to 15, further comprising the steps of inputting into the programmed computer through the input device data comprising a genotype of a bovine; correlating a physical characteristic predicted by the genotype using the processor and the data storage system; and outputting to the output device the physical characteristic correlated to the genotype for a bovine or population of bovines, and feeding the animal(s) a diet based upon the physical characteristic, thereby improving bovine production.

17. The computer-assisted method according to any one of paragraphs 10 to 16 for optimizing efficiency of feedlots for livestock comprising outputting to the output device the breeding and veterinary history of the bovine or herd of bovines and feeding the animal(s) a diet based upon their breeding and veterinary histories, thereby optimizing efficiency of feedlots for the bovine or herd of bovines.

18. A method of transmitting data comprising transmission of information from such methods according to any one of paragraphs 10 to 16, selected from the group consisting of telecommunication, telephone, video conference, mass communication, a presentation, a computer presentation, a POWERPOINT™ presentation, internet, email, and documentary communication.

19. An interactive computer system according to any one of paragraphs 10 to 16 for tracking breeding and welfare histories of cows comprising breeding and veterinarian data corresponding to a bovine or herd of bovines, and wherein the computer system is configured to allow the operator thereof to exchange data with the device or a remote database.

20. The interactive computer system according to paragraph 19, wherein the input and output devices are a personal digital assistant or a pocket computer.

21. A method of doing business for tracking breeding and welfare histories of livestock comprising breeding and veterinarian data corresponding to one or more livestock animals comprising providing to a user the computer system of paragraph 19.

22. A method of doing business for tracking breeding and welfare histories of livestock comprising breeding and veterinarian data corresponding to one or more livestock animals comprising providing to a user the computer system of paragraph 20.

23. The method of doing business according to paragraph 21, further comprising providing the animal owner or customer with sample collection equipment, such as swabs and tags useful for collecting samples from which genetic data may be obtained, and wherein the tags are optionally packaged in a container which is encoded with identifying indicia.

24. The method of doing business according any one of paragraphs 10 to 16, wherein the computer system further comprises a plurality of interactive devices and wherein the method further comprises the steps of a receiving data from the interactive devices, compiling the data, outputting the data to indicate the response of a student or class of students to a question relating to the operation of the computer-assisted method, and optionally modifying the operation of the computer-assisted method in accordance with the indication of the response.

25. The method of any one of paragraphs 10 to 24 wherein the data comprises presence or absence of one or more of a single nucleotide polymorphism(s) of interest in the FABP gene.

26. The method of paragraph 25 wherein the single nucleotide polymorphism(s) of interest is selected from the group consisting of G to C substitution at the 7516 nucleotide position of the FABP4 gene and a G to C substitution at position 7713 of the FABP4 gene.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method for identifying a bovine animal having a higher ribeye area (REA) per hundred weight hot carcass weight (cwt-HCW) as compared to the general population of bovine animals, comprising:
   (a) obtaining a biological sample from said bovine animal, said biological sample comprising nucleic acids encoding the bovine fatty acid binding protein 4("FABP4") gene from said bovine;
   (b) detecting in said nucleic acids the presence of a C in one or both alleles of the FABP4 gene at position corresponding to position 7516 of SEQ ID NO: 1; and
   (c) correlating the presence of the nucleic acid content of (b) with a higher ribeye area (REA) per hundred weight hot carcass weight (cwt-HCW) in said bovine animal.

2. The method of claim 1 further comprising sub-grouping animals according to genotype, wherein the animals of each sub-group have the same polymorphism in the FABP4 gene, said method comprising:
   (a) determining the genotype of each animal to be sub-grouped by determining the presence of a single nucleotide polymorphism in the FABP4 gene according to the method of claim 1, and
   (b) segregating individual animals into sub-groups depending on whether the animals have, or do not have, the single nucleotide polymorphism of interest in the FABP4 gene.

* * * * *